US008741891B1

(12) United States Patent  
Mash

(10) Patent No.: US 8,741,891 B1
(45) Date of Patent: *Jun. 3, 2014

(54) N-SUBSTITUTED NORIBOGAINE PRODRUGS

(75) Inventor: Deborah C. Mash, Miami, FL (US)

(73) Assignee: DemeRx, Inc., Ft. Lauderdale, FL (US)

( * ) Notice: Subject to any disclaimer, the term of this patent is extended or adjusted under 35 U.S.C. 154(b) by 173 days.

This patent is subject to a terminal disclaimer.

(21) Appl. No.: 13/165,626

(22) Filed: Jun. 21, 2011

Related U.S. Application Data

(60) Provisional application No. 61/357,479, filed on Jun. 22, 2010, provisional application No. 61/419,770, filed on Dec. 3, 2010.

(51) Int. Cl.
*A61K 31/55* (2006.01)
*C07D 471/22* (2006.01)

(52) U.S. Cl.
USPC ..................... 514/214.02; 540/579

(58) Field of Classification Search
USPC ..................... 514/214.02; 540/579
See application file for complete search history.

(56) References Cited

U.S. PATENT DOCUMENTS

| 2,813,873 A | 11/1957 | Janot et al. |
| 3,516,989 A | 6/1970 | Sallay |
| 3,557,126 A | 1/1971 | Sallay |
| 3,574,220 A | 4/1971 | Sallay |
| 3,639,408 A | 2/1972 | Nagata et al. |
| 3,715,361 A | 2/1973 | Epstein et el |
| 3,875,011 A | 4/1975 | Rubenstein et al. |
| 4,107,288 A | 8/1978 | Oppenheim et al. |
| 4,272,541 A | 6/1981 | Kotick et al. |
| 4,375,414 A | 3/1983 | Strahilevitz |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,806,341 A | 2/1989 | Chien et al. |
| 4,857,523 A | 8/1989 | Lotsof |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,935,975 A | 8/1999 | Rose et al. |
| 6,211,360 B1 | 4/2001 | Glick et al. |
| 6,291,675 B1 | 9/2001 | Coop et al. |
| 6,348,456 B1 | 2/2002 | Mash et al. |
| 6,451,806 B2 | 9/2002 | Farrar |
| 6,806,291 B1 | 10/2004 | Sunkel et al. |
| 6,864,271 B2 | 3/2005 | Bazan et al. |
| 7,220,737 B1 | 5/2007 | Mash |
| 7,737,169 B2 | 6/2010 | Corrie et al. |
| 7,745,479 B2 | 6/2010 | Nettekoven et al. |
| 7,754,710 B2 | 7/2010 | Mash |
| 8,178,524 B2 | 5/2012 | Mash |
| 8,362,007 B1 * | 1/2013 | Mash et al. ............... 514/214.02 |
| 2003/0153552 A1 | 8/2003 | Mash et al. |
| 2003/0158202 A1 | 8/2003 | Caldirola et al. |
| 2006/0051317 A1 | 3/2006 | Batrakova et al. |
| 2010/0311722 A1 | 12/2010 | Mash |
| 2010/0311723 A1 | 12/2010 | Mash |
| 2010/0311725 A1 | 12/2010 | Mash |
| 2012/0083485 A1 | 4/2012 | Mash |
| 2013/0072472 A1 | 3/2013 | Gless et al. |

FOREIGN PATENT DOCUMENTS

| CA | 2039197 | 9/1995 |
| DE | 22 17 132 | 10/1972 |
| GB | 0 841 697 | 7/1960 |

(Continued)

OTHER PUBLICATIONS

U.S. Appl. No. 13/104,406, filed May 10, 2011, Mash et al.
U.S. Appl. No. 13/165,626, filed Jun. 21, 2011, Mash, Deborah C.
U.S. Appl. No. 13/165,639, filed Jun. 21, 2011, Mash et al.
U.S. Appl. No. 13/165,642, filed Jun. 21, 2011, Mash et al.
U.S. Appl. No. 13/198,593, filed Nov. 7, 2011, Mash et al.
U.S. Appl. No. 13/383,405, To Be Decided, Moriarty, Robert.
U.S. Appl. No. 13/496,185, To Be Decided, Mash, Deborah C.
Ala-Hurula et al. "Erogotamine Abuse: Results of Ergotamine Discontinuation, with Special Reference to the Plasma Concentrations", Cephalalgia, 2/4: abstract only, 1982.
Ala-Hurula et al. "Tolfenamic Acid and Ergotamine Abuse", Headache: The Journal of Head and Face Pain, 21(6): abstract only, 1981.
Alexander. "A Procedure for Drug Screening Without the Need to Transport Urines Use of Ion Exchange Papers and Hem Agglutination Inhibition", Clin Toxicol, 9(3): abstract only, 1976.

(Continued)

*Primary Examiner* — Brenda Coleman
(74) *Attorney, Agent, or Firm* — Foley & Lardner LLP

(57) ABSTRACT

This invention relates generally to prodrugs of noribogaine. This invention also relates to pharmaceutical compositions comprising the prodrugs of noribogaine as well as method of treating pain, addiction and/or stress using such compounds and/or pharmaceutical compositions.

18 Claims, No Drawings

(56) References Cited

FOREIGN PATENT DOCUMENTS

| GB | 0 924 042 | | 4/1963 |
|---|---|---|---|
| GB | 1 256 914 | | 12/1971 |
| GB | 1 378 348 | | 12/1974 |
| GB | 2 271 059 | | 4/1994 |
| JP | 04-221315 | | 8/1992 |
| WO | WO-91/18609 | A1 | 12/1991 |
| WO | WO-93/20825 | A1 | 10/1993 |
| WO | WO-93/25217 | A1 | 12/1993 |
| WO | WO-94/06426 | A1 | 3/1994 |
| WO | WO-94/14490 | A1 | 7/1994 |
| WO | WO-96/03127 | A1 | 2/1996 |

OTHER PUBLICATIONS

Alim et al. "Open-Label, Dose Run-Up Study of Diethylpropion in Initial Cocaine Abstinence", Clinical Neuropharmacology, 17(2): abstract only, 1994.
Almeida. "Use and Abuse of Alcohol and Drugs a Clinical Study of Certain Aspects of Their Interrelationship", Bol of Sanit Panam, 88(1), abstract only, 1980.
Al-Shabanah et al. "Gastric Antiulcer and Cytoprotective Effects of Cathinone, a Psychoactive Alkaloid of Khat (Catha Edulis Forsk.) and Amphetamine in Rats", Regulatory Peptides, abstract only, 1994.
Azevedo et al. "Adrenergic Nerve Degeneration Induced by Condensation Products of Adrenaline and Acetaldehyde", Naunyn-Schmiedeberg's Arch Pharmacol, 300(2): abstract only, 1977.
Bagal et al. "Modulation of Morphine-Induced Antinociception by Ibogaine and Noribogaine", Brain Research, 741(1-2): pp. 258-262, 1996.
Ban. "Adverse Effects to Psychotomimetics. Proposition of a Psychopharmacological Classification", in: Radouco-Thomas S, ed. Pharmacologie, Toxicologie, et abus des psychotomimetiques (hallucinogens)., QV 109: abstract only, 1974.
Bartlett et al. "The Alkaloids of Tabernanthe iboga. Part IV..sup.1 The Structures of Ibogamine, Ibogaine, Tabernanthine and Voacangine", J. Am. Chem. Soc., 80: pp. 126-136, 1958.
Batrakova. "Pluronic P85 Enhances the Delivery of Digoxin to the Brain: In Vitro and In Vivo Studies", The J. of Pharm. and Exp. Thera, 296, p. 551-557, 2001.
Baumann et al. "Comparative Neurobiology of Ibogaine and its Metabolite, 12-Hydroxyibogaimine (Noribogaine), in Rodents." Conference at New York University, Abstract only, 2000.
Beaubrun. "The Diagnosis and Management of Acute Psychotic Reaction Due to Alcohol and Drugs", Caribb Med J, 36(1): abstract only, 1975.
Beck et al. "Energy-Dependent Reduced Drug Binding as a Mechanism of Vinca Alkaloid Resistance in Human Leukemic Lymphoblasts", Mol Pharmacol, 24(3): abstract only, 1983.
Benet et al. "Pharmacokinetics: Biotransformation of Drugs." In Gilman et al. Goodman and Gilman's the Pharmacological Basis of Therapeutics (1990) :13-16.
Benoist et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunol Immunother, 30(5): abstract only, 1989.
Bert et al. "Non-Amphetaminic Central Stimulation by Alkaloids from the Ibogaine and Vobasine Series", Planta Med., 54(3): abstract only, 1988.
Bhargava et al. "Effects of ibogaine and noribogaine on the antinociceptive action of mu-, delta- and kappa-opioid receptor agonists in mice", Brain Research 752:234-238, 1997.
Blum et al. "Peyote a Potential Ethnopharmacologic Agent for Alcoholism and Other Drug Dependencies Possible Biochemical Rationale", Clin Toxicol, 11(4): abstract only, 1977.
Blum et al. "Possible Role of Tetrahydroisoquinoline Alkaloids in Postalcohol Intoxication States", Ann N Y Acad Sci, 273: abstract only, 1976.

Blum et al. "Putative Role of Isoquinoline Alkaloids in Alcoholism: A Link to Opiates", Alcohol Clin Exp Res, 2(2):abstract only, 1978.
Brady et al. "Analgesic Effects of Intraventricular Morphine and Enkephalins in Nondependent and Morphine-Dependent Rats", J. Pharmacol. Exp. Ther., 222(1): abstract only, 1982.
Buchi et al. "The total synthesis of iboga alkaloids", J. Am. Chem. Soc. vol. 88, p. 3099-3109, 1966.
Bundgaard. "Design of Prodrugs: Bioreversible Derivatives for Various Functional Groups and Chemical Entities." Design of Prodrugs, 1-10, 1985.
Bussel et al. "Isolated Thrombocytopenia in Patients Infected with HIV Treatment with Intravenous Gamma Globulin", Am J Hematol, 28(2): abstract only, 1988.
Caldwell et al. "The Biochemical Pharmacology of Abused Drugs. III. Cannabis, Opiates, and Synthetic Narcotics", Clin. Pharmacol. Ther., 16/6: abstract only, 1974.
Cankat. "Pharmacological Aspects of Drug Induced Headache", Funct. Neurol., 7/6: abstract only, 1992.
Cappendijk et al. "Inhibitory Effects of Ibogaine on Cocaine Self-Administration in Rats", Eur. J. Pharmacol., 241 (2-3): abstract only, 1993.
Cappendijk et al. "The Inhibitory Effect of Norharman on Morphine Withdrawal Syndrome in Rats: Comparisons with Ibogaine", Behavioural Brain Research, pp. 1-3, 1994.
Castle. "Drugs and Fibrotic Reactions—Part I", Adverse Drug React. Bull., 113: abstract only, 1985.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 75.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny et al. "Opioid responsiveness of cancer pain syndromes caused by neuropathic or nociceptive mechanisms: a combined analysis of controlled, single-dose studies", Neurobiology 44:857-861, 1994.
Cheze et al. "Determination of ibogaine and noribogaine in biological fluids and hair by LC-MS/MS after Tabernanthe iboga abuse", Forensic Science International, Elsevier Scientific Publishers Ireland Ltd, IE, vol. 176. No. 1, pp. 58-66,2007.
Criel et al. "Drug Dependent Red Cell Antibodies and Intravascular Haemolysis Occurring in Patients Treated with 9 Hydroxy-Methyl-Ellipticinium", Br J Haematol, 46(4): abstract only, 1980.
Damstrup et al. "Retroperitoneal Fibrosis After Long-Term Daily Use of Ergotamine", Int. Urol. Nephrol., 18/3: abstract only, 1986.
Deecher et al. "Mechanisms of Action of Ibogaine and Harmaline Congeners Based on Radioligand Binding Studies", Brain Research, 571(2): pp. 242-247, 1992.
Diener et al. "Analgesic-Induced Chronic Headache Long-Term Results of Withdrawal Therapy", J Neurol, 236(1):abstract only, 1989.
Dierckx et al. "Intraarterial Sodium Nitroprusside Infusion in the Treatment of Severe Ergotism", Clin. Neuropharmacol., 9/6: abstract only, 1986.
Dzoljic et al. "Effect of Ibogaine on Naloxone-Precipitated Withdrawal Syndrome in Chronic Morphine-Dependent Rats", Arch. Int. Pharmacodyn., 294:64-70, 1988.
Eberwine et al. "Molecular Analysis of Cellular Responses to Opiate Use", Fidia Res. Found. Symp. Ser., 7(Neurotransm. Regul. Gene Transcr.): abstract only, 1991.
Elkind, "Drug Abuse and Headache", Med Clin North Am, 75(3): abstract only, 1991.
Evenson. "Developments in Therapeutic Drug Monitoring and Alkaloid Analysis", Fed Proc, 34(12): abstract only, 1975.
Faglia et al. "Dihydroergocryptine in Management of Microprolactinomas", J Clin Endocrinol Metab, 65(4): abstract only, 1987.

(56) References Cited

OTHER PUBLICATIONS

Fairchild et al. "Keynote Address: Multidrug Resistance: A Pleiotropic Response to Cytotoxic Drugs", Int. J. Radiat. Oncol. Biol. Phys., 20/2; abstract only, 1991.
Finkle. "Phencyclidine Identification by Thin-Layer Chromatography. A Rapid Screening Procedure for Emergency Toxicology", Am. J. Clin. Pathol., 70/2: abstract only, 1978.
Fonne-Pfister et al. "Xenobiotic and Endobiotic Inhibitors of Cytochrome P-450db1 Function, the Target of the Debrisoquine / Sparteine Type Polymorphism", Biochem. Pharmacol., 37(20): abstract only, 1988.
Frances et al. "Effects of Ibogaine on Naloxone-Precipitated Withdrawal in Morphine-Dependent Mice", Fundam Clin Pharmacol, 6(8-9): abstract only, 1992.
Gabr et al. "Changes in Absolute Amount of Alkaloids in Datura-Metel Treated with Certain Growth Regulators", Herba Pol, 21(2): abstract only, 1975.
Garcia et al. "Chronic pain states: pathophysiology and medical therapy", Seminars in Arthritis and Rheumatism, 27:1-16, 1997.
Gennaro. "Remington: The Science and Practice of Pharmacy", Mack Publishing Col., vol. II, pp. 1736 & 1814, 1995.
George et al. "Palliative medicine", Postgrad, Med. Journal, vol. 69, pp. 426-449, 1993.
Gifford et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41(4): abstract only, 1992.
Glick et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657:14-22, 1994.
Glick et al. "Effect of Ibogaine on Acute Signs of Morphine Withdrawal in Rats: Independence from Tremor", Neuropharmacology, 31/5: abstract only, 1992.
Glick et al. "Effects of Aftereffects of Ibogaine on Morphine Self-Administration in Rats", European Journal of Pharmacology, 195(3): abstract only, 1991.
Glick et al. "Ibogaine-like effects of noribogaine in rats", Brain Research, 713:294-297, 1996.
Glick et al. "Local Effects of Ibogaine on Extracellular Levels of Dopamine and Its Metabolites in Nucleus Accumbens and Striatum: Interactions with D-Amphetamine", Brain Research, 628(1-2): abstract, 1993.
Gold et al. "Effect of Methadone Dosage on Clonidine Detoxification Efficacy", Am. J. Psychiatry, 137/3: abstract only, 1980.
Gothoni. "Harmine-, Lon-954- and 5-Hydroxytryptophan-Induced Tremors in Rats Withdrawn from Ethanol", Acta Pharmacol Toxicol, 57(1): abstract only, 1985.
Gross. "Effect of Ergot Alkaloids on Serum Prolactin in Non-Psychotic Organic Brain Syndrome of the Elderly", Exp Aging Res, 5(4): abstract only, 1979.
Gunn. "Relations Between Chemical Constitution, Pharmacological Actions, and Therapeutic Uses, in the Harmine Group of Alkaloids", From the Pharmacological Laboratory, University of Oxford:379-396, 1935.
Haber et al. "Tetrahydroisoquinolines—Endogenous Products After Chronic Alcohol Abuse", Pharmazie, 47/1: abstract only. 1992.
Halikas et al. "Treatment of Crack Cocaine Use with Carbamazepine", Am J Drug Alcohol Abuse, 18(1): abstract only, 1992.
Hanks. "Opioid-responsive and opioid-non-responsive pain in cancer", British Medical Bulletin 47:718-731, 1991.
Hardman et al. "Goodman & Gilman's The Parmacological Basis of Therapeutics" (9th ed, 1996) p. 51 and 57-58.
Harsing, Jr. et al. "Evidence that Ibogaine Releases Dopamine from the Cytoplasmic Pool in Isloated Mouse Striatum", Journal of Neural Transmission General Section, 96(3):abstract only, 1994.

Hearn et al. "Identification and Quantitation of Ibogaine and an o-Demethylated Metabolite in Brain and Biological Fluids Using Gas Chromatography-Mass Spectrometry." J. Analytical Toxicology, 19:427-434, 1995.
Heel et al. "Buprenorphine: A Review of Its Pharmacological Properties and Therapeutic Efficacy", Drugs, 17(2): abstract only, 1979.
Henry et al. "Reversible Cerebral Arteriopathy Associated with the Administration of Ergot Derivatives", Cephalalgia, 4/3: abstract only.
Ho et al. "Metabolism of Harmaline in Rats." Biochemical Pharmacology, 20:1313-1319, 1971.
Hoes. "Clinical Criteria for the Selection of Anxiolytics", Tijdschr. Ther. Geneesm. Onderz., 9/9: abstract only, 1984.
Holbrook. "Nicotine Addiction." In Isselbacher et al. Harrison's Principles of Internal Medicine:2433-2437, 1994.
Holzner et al. "The Neuroleptic Sleeping Course in Chronic Headache", Therapiewoche, 35/36: abstract only, 1985.
Huang et al. "Cytotoxicity and Sister Chromatid Exchanges Induced in Vitro by Six Anticancer Drugs Developed in the People's Republic of China", J Natl Cancer Inst, 71(4): abstract only, 1983.
Hubens et al. "Chronic Intake of a Hydrogenated Ergot Alkaloid Causing Peripheral Vascular Ischemia—A Case Report", Vasc. Surg., 21/4: abstract only, 1987.
Huffman et al. "A Formal Synthesis of (±)-Ibogamine", J. Org. Chem. vol. 50, pp. 1460-1464, 1985.
Isler. "Treatment of Headache", Schweiz. Med. Wochenschr., 114/35: abstract only, 1984.
Jaffe. "Drug Addiction and Drug Abuse." In Gilman et al. Goodman and Gilman's The Pharmacological Basis of Therpeutics:522-523, 559-568, 1990.
Jaffe. "Psychopharmacology and Opiate Dependence", U.S. Public Health Serv. Publ., 1957-1967:1836, 1967.
Jane et al. "High-Performance Liquid Chromatographic Analysis of Basic Drugs on Silica Columns Using Non-Aqueous Ionic Eluents. II. Application of UV, Fluorescence and Electrochemical Oxidation detection", J. Chromatogr., 323(2): abstract only, 1985.
Jansen et al. "Ethnopharmacology of Kratom and the Mitragyna Alkaloids", J Ethnopharmacol, 23(1): abstract only 1988.
Janzen. "Historyof Use of Psychotropic Drugs in Central Africa", Psychotropes, 1/2: abstract only, 1983.
Justins. "Management strategies for chronic pain", Annals of the Rheumatic Diseases, vol. 55, pp. 588-596, 1996.
Kalix. "Khat: A Plant with Amphetamine Effects", J Subst Abuse Treat, 5(3): abstract only, 1988.
Kalix. "Pharmacological Properties of the Stimulant Khat", Pharmacol. Ther., 48/3: abstract only, 1990.
Keefner. "A Gas Chromatography-Mass Spectrometry (GOMS) Method for Ibogaine", Society for Neuroscience Abstracts, 19(1-3): abstract only, 1993.
Keller et al. "Modulation of Neopterin Release by Human Kupffer Cells in Culture: Possible Implication in Clinical Monitoring of HIV-Seropositive Subjects", Cells Hepatic Sinusoid, 3: abstract only, 1991.
Knoll. "Azidomorphines and Homopyrimidazols: A New Approach to the Ideal Analgetic", Acta Physicol Pharmacol Bulg, 3(2): abstract only, 1977.
Knoll. "Azidomorphines: A New Family of Potent Analgesics with Low Dependence Capacity", Prog. Neuro-Psychopharmacol., 3/1-3: abstract only, 1979.
Koch et al. "Drug-Induced Liver Injury in Liver Biopsies of the Years 1981 and 1983, their Prevalence and Type of Presentation", Path. Res. Pract., 179: abstract only, 1985.
Konig. "Psychiatric Intensive Therapy After Acute Alkaloid Withdrawal Syndrome", Infusionsther Klin Ernahr, 6(1): abstract only, 1979.
Kornetsky, "Pharmacology Drugs Affecting Behavior", New York, John Wiley & Sons, pp. 186-187, 1976.
Kostowski et al. "The Effects of Some Hallucinogens on Aggressiveness of Mice and Rats" Pharmacology vol. 7, pp. 259-263, 1972.
Krug. "Cocaine Abuse: Historical, Epidemiologic, and Clinical Perspectives for Pediatricians", Advances in Pediatrics, 36:369-406, 1989.

(56) References Cited

OTHER PUBLICATIONS

Kupers et al., "Morphine differentially affects the sensory and affective pain ratings in neuorgenic and idiopathic forms of pain." Pain 47:5-12, 1991.
Lakoski et al. "Electrophysiologic Characterization of an Ibogaine Metabolite in Dorsal Raphe Nucleus and Hippocampus." Soc. Neurosc. 21:716 Abstract only, 1995.
Larson-Prior et al. "Electrophysiologic Characterization of an Ibogaine Metabolite in the Cerebellar Cortex." Soc. Neurosc. 21:716 Abstract pnly, 1995.
Lemontt et al. "Increase MDR Gene Expression and Decreased Drug Accumulation in Multidrug-Resistant Human Melanoma Cells", Cancer Res, 48(22): abstract only, 1988.
Leoni et al. "Effect of Cocaine and Morphine on Neutral Endopeptidase Activity of Human Peripheral Blood Mononuclear Cells Cultures with Lectins", Cell Biochem Funct, 11(3): abstract only, 1993.
Lerida et al. "Incidence of Morphine Withdrawal and Quasi-Abstinence Syndrome in a Model of Chronic Pain in the Rat", Neurosci., 81(1-2): abstract only, 1987.
Lewis et al. "Adverse Reactions and Interactions with .beta.-Adrenoceptor Blocking Drugs", Med. Toxicol., 1/5: abstract only, 1986.
Lewis et al. "Narcotic Analgesics and Antagonists", Annu Rev Pharmacol, 11: abstract only, 1971.
Licht et al. "Induction of Multiple-Drug Resistance During Anti-Neoplastic Chemotherapy In-Vitro", Int J Cancer, 49(4): abstract only, 1991.
Ling et al., "Drugs of Abuse-Opiates", in Addtiction Medicine [Special Issue], Western Journal of Medicine, 152:565-572, 1990.
Low et al. "Effects of Acronycine and Cytouchalasin B on the Division of Rat Leukemia Cells", Exp Cell Res, 131(1): abstract only, 1981.
Ma et al. "Inhibition of Respiratory Burst Activity in Alveolar Macrophages by Bisbenzylisoquinoline Alkaloids: Characterization of Drug-Cell Interaction", Exp. Lung Res., 18/6: abstract only, 1992.
Maisonneuve et al. "Interactions of Ibogaine and D-Amphetamine: in vivio Microdialysis and Motor Behavior in Rats." Brain Research 579:87-92, 1992.
Maisonneuve et al. "Acute and Prolonged Effects of Ibogaine on Brain Dopamine Metabolism and Morphine-Induced Locomotor Activity in Rats", Brain Research, 575(1): abstract only, 1992.
Maisonneuve et al. "Interactions Between Ibogaine, a Potential Anti-Addictive Agent, and Morphine: an in Vivo Microdialysis Study", Eur. J. Pharmacol., 199(1): abstract only, 1991.
Martellotta et al. "Effects of the Calcium Antagonist Isradipine on Cocaine Intravenous Self-Administration in Rats", Psychopharmacologia, 113(3-4): Abstract only, 1994.
Martin et al. "Neuropathic Pain in Cancer Patients: Mechanisms, Syndromes, and Clinical Controversies," Journal of Pain and Symptom Management 14(2):99-117, 1997.
Mash et al, "Properties of Ibogaine and its Principle Metabolite (12-hydroxyibogamine) at the MK-801 binding site of the NMDA receptor complex," Neuroscience Letters, 192, 53-56, 1995.
Mash et al. "Ligand Binding Profiles of Ibogaine and its O-demethylated Metabolite Noribogaine: Implications for Developing Novel Multi-target Anti-addiction Agents." Soc. Neurosc. (1995) 21:717 Abstract only.
Mash et al. "Preclinical screening of an ibogaie metabolite (noribogaine) on cocaine-induced hyperlocomotion and cocaine self-administration." Soc. Neurosc. 22:1929 Abstract only, 1996.
Mash et al. "Ibogaine in the Treatment of Heroin Withdrawal," The Alkaloids 56:1-17, 2001.
Mateer et al. "Reversible Ipecac Myopathy", Arch. Neurol., 42/2: abstract only, 1985.
Matharu et al. "Preformulation and Development of Ibogaine Injection for the Treatment of Drug Abuse", Pharmaceutical Research, 10: abstract only, 1993.

Mattingly et al. "Selective Antagonism of Dopamine D Sub1 and D Sub 2 Receptors Does Not Block the Development of Behavioral Sensitization to Cocaine", Psychopharmacologia, 114(2): abstract only, 1994.
McNeish et al. "The 5-HT Sub 3 Antagonist Zacopride Attenuates Cocaine-Induced Increases in Extracellular Dopamine in Rat Nucleus Accumbens", Pharmacology, Biochemistry, and Behavior, 45(4): abstract only, 1993.
Melchior et al. "Preference for Alcohol Evoked by Tetra Hydro Papaveroline Chronically Infused in the Cerebral Ventricle of the Rat", Pharmacol Biochem Behav, 7(1): abstract only, 1977.
Mendelson et al. "Cocaine and Other Commonly Abused Drugs." In Isselbacher et al. Harrison's Principles of Internal Medicine:2429-2433, 1994.
Menzies et al. "Gangrene of the Small Bowel: A Complication of Methysergide Therapy", Aust. N. Z. J. Surg., 52/5: abstract only, 1982.
Metelitsa. "Pharmacological Agents in Controlling Smoking", Biull Vsesoiuznogo Kardiol Nauchn Tsentra, 10(1): abstract only, 1987.
Millan, "k-Opioid Receptors and Analgesia," Trendes in Pharmacologicla Sciences, 11, pp. 70-76, 1990.
Mizuhashi et al. "Antitumor Activities of IKP-104 A 4-1H Pyridizinone Derivative on Cultured and Implanted Tumors", Jpn J Cancer Res, 81(12): abstract only, 1990.
Montefiori et al. "In Vitro Evaluation of Mismatched Double-Stranded RNA (Ampligen) for Combination Therapy in the Treatment of Acquired Immunodeficiency Syndrome", AIDS Res Hum Retroviruses, 5(2); abstract only, 1989.
Mulamba et al., Alcaloides de Tabernanthe Pubescens. Journal of Natural Products, vol. 44, No. 2, p. 184-189, 1981.
Naranjo. "Ibogaine in psychotherapy: psychoanalysis according to Naranjo", part IV, pp. 1-2. http://www.nettuno.it/fiera/electric.italy/bwitif:html, 1993.
Nishiyama et al. "Expression of the Multidrug Transporter, P-Glycoproteiin, in Renal and Transitional Cell Carcinomas", Cancer, 71(11):3611-3619, 1993.
Nooter et al. "Multidrug Resistance (MDR) Genes in Haematological Malignancies", Cytotechnology, 12(1-3): abstract only, 1993.
Nunn-Thompson et al. "Pharmacotherapy for Making Cessation", Clin Pharm, 8(10): abstract only, 1989.
Obach et al., "Cythochrome P4502D6 Catalyzes the O-Demethylation of the Psychoactive Alkaloid Ibogaine to 12-Hydroxyibogamine" Drug Metabolism and Disposition 26(8):764-768, 1998.
O'Hearn et al. "Degenration of Prukinje Cells in Parasagittal Zones of the Cerebellar Vermis After Treatment with Ibogaine of Harmaline", Neuroscience, 55(2): abstract only, 1993.
O'Hearn et al. "Ibogaine Induces Glial Activation in Parasagittal Zones of the Cerebellum", Neuroreport, 4/3: abstract only, 1993.
Pablo et al, "Noribogaine Stimulates Naloxone-Sensitive[35S]GTPgammaS Binding," NeuroReport, 9, pp. 109-114. (Website Publication Date of Dec. 20, 1997.), 1998.
, , D145 Pacifici et al. "Immunological Effect of Cocaine and Host Resistance in Mice", Int J Immunother, 8(2): abstract only, 1992.
Palyi. "Survivial Responses to New Cytostatic Hexitols of P388 Mouse and K562 Leukemia Cells in Vitro", Cancer Treat. Rep., 70(2): abstract only, 1986.
Pantazis et al. "Efficacy of Camptothecin Congeners in the Treatment of Human Breast Carcinoma Xenografts", Oncology Research, 5(8): abstract only, 1994.
Pehek. "Effects of Cathinone and Amphetamine on the Neurochemistry of Dopamine in Vivo", Neuropharmacology, 29/12: abstract only, 1990.
Perera et al. "Tertiary Indole Alkaloids of Tabernaemontana Dichotoma Seeds", Planta Med., 49/1: abstract only, 1983.
Perrin. "Clinical Pharmacokinetics of Ergotamine in Migraine and Cluster Headache", Clin. Pharmacokin., 10/4: abstract only, 1985.
Popik et al. "NMDA Antagonist Properties of the pUtative Antiaddictive Drug, Ibogaine", Journal of Pharmaceutical and Experimental Therapeutics, 275(2), 753-760, 1995.
Popik et al. "The Putative Anti-Addictive Drug Ibogaine is a Competitive Inhibitor of ( SUP 3 H) Binding to the NMDA Receptor Complex", Psychopharmacologia, 114(4): abstract only, 1994.

(56) References Cited

OTHER PUBLICATIONS

Popik et al. "100 Years of Ibogaine: Neurochemical and Pharmacological Actions of a Putative anti-addictive Drug", Pharmacological Reviews 47(2), pp. 235-253, 1995.
Pulvirenti et al. "Lisuride Reduces Intravenous Cocaine Self.-Administration in Rats", Pharmacology, Biochemistry and Behavior, 47(4): abstract only, 1994.
Qiu et al. "The Influence of Chronic Nicotine Treatment on Stress-Induces Gastric Ulceration and Emptying Rate in Rats", Experientia, 48(4): abstract only, 1992.
D156 Rezvani et al. "Noribogaine, a Primary Ibogaine Metabolite, Reduces Alcohol Intake in P and Fawn-Hooded Rats." RSA Annual Scientific Meeting Abstract only, 1995.
Rezvani et al. "Reduction of Alcohol Intake in Alcohol Preferring Fawn-hooded and P Rats by Noribogaine, the Primary Metabolite of Ibogaine." NIDA Monograph Series (1996) 162:281 Abstract only.
Ricceri et al. "Postnatal cocaine Esposure Affects Neonatal Passive Avoidance Performance and Cholinergic Development in Rats", Pharmacology, Biochemistry and Behavior, 45(2): abstract only, 1993.
Rodriguez et al. "Cocaine Adminstration Prior to Reactivation Facilitates Later Acquisition of an Avoidance Response in Rats", Psychopharmacologia, 112(2-3): abstract only, 1993.
Rosenmund et al. "Ibogamin, Ibogain and Epiibogamin" Chem. Ber. vol. 108, p. 1871-1895, 1975. structures and abstract only.
Sachs et al. "Corneal Complications Associated with the Use of Crack Cocaine", Ophthalmology, 100(2): abstract only, 1993.
Salmoiraghi et al. "Effects of LSD 25, BOL 148, Bufotenine, Mescaline and Ibogaine on the Potentiation of Hexobarbital Hypnosis Produced by Serotonin and Reserpine." J. Pharm and Exp Ther. vol. 120. No. 1, pp. 20-25, 1957.
D163 Samadi-Baboli et al. "Preparation of Low Density Lipoprotein-9-Methoxy-Illipticin Complex and Its Cytotoxic Effect Against L1210 and P388 Leukemic Cells in Vitro", Eur J Cancer Clin Oncol, 25(2): abstract only, 1989.
Saper et al. "Ergotamine Tartrate Dependency: Features and Possible Mechanisms", Clin. Neuropharmacol., 9/3: abstract only, 1986.
Schecter et al. "Comparison of the Behavioral Effects of Ibogaine from Three Sources: Mediation of Discriminative Activity", European Jornal of Pharmacology, 249(1): abstract only, 1993.
Schneider et al. "Analysis of the Cardiovascular Action of Ibogaine Hydrochloride (1)" Arch. Int. Pharmacodyn. vol. 110, pp. 92-102, 1957.
Schneider et al., Neuropharmacological Studies of Ibogaine: An Indole Alkaloid with Central Stimulant Properties Ann. of N.Y. Acad. Sci. vol. 66, pp. 765-776, 1957.
Schneider et al., "Potentiation Action of Ibogaine on Morphine Analgesia" Experiential vol. 12, pp. 323-324, 1956.
Schnider et al. "Use and Abuse of Analgesics in Tension-Type Headache", Cephalalgia, 14/2: abstract only, 1994.
Schuckit et al. "Opioid Drug Use." In Isselbacher et al. Harrison's Principles of Internal Medicine:2425-2429, 1994.
Schuckit. "Alcohol and Alcoholism." In Isselbacher et al. Harrison's Principles of Internal Medicine:2420-2425, 1994.
Seeber et al. "In Vivo Resistance Towards Anthracyclines, Etoposide, and Cis-Diamminedichloroplatinum (II)", Cancer Res., 42(11):abstract only, 1982.
Sehested et al. "The Carboxylic Ionophore Monensin Inhibits Active Drug Efflux and Modulates In-Vitro Resistance in Daunorubicin Resistant Enrlich Ascites Tumor Cells", Biochem Pharmacol, 37(17): abstract only, 1988.
Sershen et al. "Ibogaine Antagonizes Cocaine-Induced Locomotor Stimulation in Mice", Life Sci., 50(15): abstract only, 1992.
Sershen et al. "Ibogaine Reduces Amphetamine-Induced Locomotor Stimulation in C57BL/6By Mice, but Stimulates Locomotor Activity in Rats", Life Sci., 51(13): abstract only, 1992.
Sershen et al. "Ibogaine Reduces Preference for Cocaine Consumption in C57BL/6By Mice", Pharmacol., Biochem. Behav., 47(1): abstract only, 1994.

Shen et al. "Antagonists at Excitatory pioid Receptors on Sensory Neurons in Culture Increase Potency and Specificity of Opiate Analgesics and Attenuate Development of Tolerance / Dependence", Brain Research, 636(2): abstract only, 1994.
Sheppard. "A Preliminary Investigation of Ibogaine: Case Reports and Recommendations for Further Study", J. Subst. Abuse Treat., 11/4: abstract only, 1994.
D179 Shir et al., "Neuropathic pain unrelieved by morphine, alleviated by haloperidol" Harefuah 118(8):452454, Abstract only, 1990.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula et al. "Rationale for Design for Biologically Reversible Drug Derivatives: Prodrugs." Journal of Pharmaceutical Sciences, 64(2):181-210, 1975.
Slotkin et al. "A Model of Harmine Metabolism in the Rat." The Journal of Pharmacology and Experimental Therapeutics, 174(3):456-462, 1970.
Slotkin et al. "Blood Levels and Urinary Excretion of Harmine and its Metabolites in Man and Rats." The Journal of Pharmacology and Experimental Therapeutics, 173(1):26-30, 1970.
Slotkin et al. "Urinary Metabolites of Harmine in the Rat and their Inhibition of Monoamine Oxidase." Biochemical Pharmacology 19:125-131, 1970.
Sloviter et al. "A Common Mechanism of Lysergic Acid, lndolealkylamine and Phenethylamine Hallucinogens: Serotonergic Mediation of Behavioral Effects in Rats" J. Pharm. Exp. Ther. vol. 214, No. 2, pp. 231-238, 1980.
Smith. "Interaction of Biogenic Amines with Ethanol", Adv Exp Med Biol, 56: abstract only, 1975.
Solinas et al. "Solid-supported reagents and catch-and-release techniques in organic synthesis". Synthesis 20070816 DE LNKD-DOI:10.1055/S-2007-983806, No. 16., pp. 2409-2453, 2007.
Stella. "Pro-drugs: An Overview and Definition." Prodrugs As Novel Drug Delivery System. ACS Symposium Series :1-115, 1975.
Stella. "Pro-drugs as Novel Drug Delivery Systems", Higuchi, T. et al., ed. (American Chemical Society, Washington), pp. 1-49, 1975.
Sugiyama et al. "Quantitative Analysis of Cell-Kill Effects of Anticancer Drugs: Consideration of Both In Vitro and In Vivo Expreimental Systems", Gan To Kagaku Ryoho, 14(12): abstract only, 1987.
Tarnower et al. "Ergotism Masquerading as Arteritis", Postgrad Med, 85(1): abstract only, 1989.
Teoh et al. "Buprenorphine Effects on Morphine- and Cocaine-Induced Subjective Responses by Drug-Dependent Men", Journal of Clinical Psychopharmacology, 14(1): abstract only, 1994.
Tfelt-Hansen et al. "Nitroglycerin for Ergotism. Experimental Studies in Vitro and in Migraine Patients and Treatment of an Overt Case", Eur. J. Clin. Pharmacol., 22/2: abstract only, 1982.
Torrenegra et al. "Alkaloids of stemmadenia grandiflora", Phytochemistry, 27(6): pp. 1843-1848, 1998.
Tsuruo. "Multidrug Resistance: A Transport System of Antitumor Agents and Xenobiotics", Princess Takamatsu Symp, 21: abstract only, 1990.
Uldry et al. "Cerebrovascular Accidents in Relation to Drug Consumption or Drug Abuse", Schweiz Rundsch Med Prax, 78(23): abstract only, 1989.
Valadez et al. "Persistence of the Ability of Amphetamine Preexposure to Facilitate Acquistion of Cocaine Self-Administration", Pharmacology, Biochemistry and Behavior, 47(1): abstract only, 1994.
Valencia et al. "Obovatine, a new bisindole alkaloid from stemmadenia obovata", Journal of Natural Products, 58(1):pp. 134-137, 1995.
Vescovi et al. "Successful Treatment of Opiate Withdrawal Using Lysine Acetylsalicylate", Curr. Ther. Res., Clin. Exp., 33/5: abstract only, 1983.
Villalba et al. "Uses and Abuses of Ipecacuana Syrup", Farm. Clin., 9/1: abstract only, 1992.
Wells et al. "Recognition and Treatment of Arterial Insufficiency from Cafergot", J. Vasc. Surg., 4/1: abstract only, 1986.

(56) References Cited

OTHER PUBLICATIONS

Whitaker et al. "High Affinity 3H-Serotonin Binding to Caudate: Inhibition by Hallucinogenic and Serotonergic Drugs", Psychopharmacology, vol. 59, pp. 1-5, 1978.

Whitaker et al., "Selective Labeling of Serotonin Receptors by d'(3H)Lysergic Acid Diethylamide in Calf Caudate", Proc. Natl. Acad. Sci., USA vol. 75, No. 12, pp. 5783-5787, 1978.

Whittaker et al. "Recurrent Laryngeal Nerve Paralysis in Patients Receiving Vincristine and Vinblastine", Br Med J, 1(6071): abstract only, 1977.

Widler et al. "Pharmacodynamics and Pharmacokinetics of Khat: a Controlled Study", Clin. Pharmacol. Ther., 55/5: abstract only, 1994.

Wildmann. "Heterocycles as Physiological Ligands for the Benzodiazepine Receptor and for Other Binding Sites", Pharmacol Res, 21(6): abstract only, 1989.

Williams, Jr. et al. "The 'Alice in Wonderland' Experience Ergot Alkaloid Therapy for Prolactin-Secreting Pituitary Tumors", West. J. Med., 138/3: abstract only, 1983.

Wishart et al. "Is Multidrug Resistance Relevant in Breast Cancer", Eur. J. Surg. Oncol., 17/5: abstract only, 1991.

Witt et al. "Pharmacodynamic and Pharmacokinetic Characterization of Poly(Ethylene glycol) Conjugation to Met-Enkephalin Analog [$^D$-Pen$^2$,$_D$-Pen$^5$]-enkephalin (DPDPE)", J. of Pharm. and Exp. Thera., 298(2), pp. 848-856, 2001.

Witt et al. "Pluronic P85 Block Copolymer Enhances Opioid Pepetide Analgesia", J. of Pharm. and Exp. Thera., 303(2), pp. 760-767, 2002.

D211 Worz. "Effects and Risks of Psychotropic and Analgesic Combinations", Am. J. Med., 75/5A: abstract only, 1983.

Zetler et al. "Pharmacokinetics in the Rat of the Hallucinogenic Alkaloids Harmine and Harmaline." Naunyn-Schmiedeberg's Arch. Pharmacol., 285, 273-292, 1974.

Zetler et al. "Cerebral Pharmacokinetics of Tremor-Producing Harmala and Iboga Alkaloids" Pharmacology vol. 7, No. 4, pp. 237-248, 1972.

James, "Linkers for solid phase organic synthesis", Tetrahedron 55, 1999, 4855-4946.

Layer, et al., "Structurally modified ibogaine analogs exhibit differing affinities for NMDA receptors," European Journal of Pharmacology, 1996, 309:159-165.

Snyder, et al., "Practical HPLC Method Development", 1997, 2nd Ed., pp. 214-218, 266, 267, 282 & 283, John Wiley & Sons, Inc.

Stahl, et al., "Handbook of Pharmaceutical Salts", 1998, p. 250 John Wiley & Sons., Inc.

\* cited by examiner

N-SUBSTITUTED NORIBOGAINE PRODRUGS

CROSS-REFERENCE TO RELATED APPLICATIONS

This application claims priority under 35 U.S.C. §119(e) to U.S. Provisional Patent Application Ser. No. 61/357,479, filed on Jun. 22, 2010, and to U.S. Provisional Patent Application Ser. No. 61/419,770, filed on Dec. 3, 2010, both of which applications are incorporated by reference herein in their entirety.

FIELD OF THE INVENTION

This invention relates generally to prodrugs of noribogaine. This invention also relates to pharmaceutical compositions comprising the prodrugs of noribogaine as well as methods of treating pain, addiction and/or stress using such compounds and/or pharmaceutical compositions.

STATE OF THE ART

Noribogaine is a well known derivative of ibogaine and is sometimes referred to as 12-hydroxyibogaine. It is a metabolite of ibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tryptamine, tetrahydrohavaine and indolazepines. Noribogaine can be depicted by the following formula:

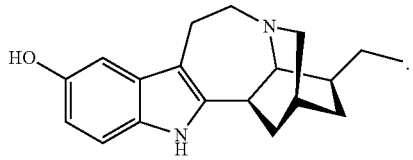

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Noribogaine is typically administered orally or intravenously and becomes systemically available to the treated patient. While noribogaine allosterically binds tightly to the µ and κ receptors, the systemic circulation of noribogaine increases the likelihood of undesirable side effects while the availability of noribogaine is limited by the efficiency of its passage across the blood brain barrier.

Accordingly, there is a need to reduce the systemic circulation of noribogaine while maintaining or increasing its concentration in the brain particularly at the µ and κ receptors.

SUMMARY OF THE INVENTION

This invention relates, in part, to a class of noribogaine prodrugs which, after administration, release noribogaine in vivo. The prodrug moiety is selected to be readily cleavable either by a cleavable linking arm or by cleavage of the prodrug entity that binds to noribogaine such that noribogaine is generated in vivo. In one preferred embodiment, the prodrug moiety is selected to facilitate binding to the µ and/or κ receptors in the brain either by facilitating passage across the blood brain barrier or by targeting brain receptors other than the µ and/or κ receptors.

Accordingly, in one embodiment, this invention is directed to compounds which are represented by Formula I below:

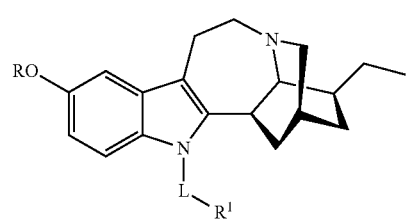

wherein L is selected from the group consisting of a covalent bond and a cleavable linker group;

R is selected from the group consisting of hydrogen, a hydrolysable group selected from the group consisting of —C(O)R$^2$, —C(O)NR$^3$R$^4$ and —C(O)OR$^5$, where R$^2$ is selected from the group consisting of hydrogen, alkyl, substituted alkyl, alkenyl, substituted alkenyl, alkynyl and substituted alkynyl, R$^3$ and R$^4$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, R$^5$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic provided that R is not a saccharide or an oligosaccharide;

R$^1$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic provided that R$^1$ is not a saccharide or an oligosaccharide;

or pharmaceutically acceptable salts thereof, provided that when L is a covalent bond and R$^1$ is hydrogen, then R is selected from the group consisting of —C(O)NR$^3$R$^4$ and —C(O)OR$^5$; and further provided that when R is hydrogen or —C(O)R$^2$ and L is a covalent bond, then R$^1$ is not hydrogen.

In one embodiment, R is hydrogen and L is a cleavable group.

In one embodiment, R is hydrogen, L is a —C(O)—, —C(O)O—, or —C(O)NH—, and R$^1$ is substituted alkyl. Preferably R$^1$ is alkyl substituted with —NR$^6$R$^7$ where R$^6$ and R$^7$ are independently selected from the group consisting of hydrogen, alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

In one embodiment, R is selected from the group consisting of —C(O)NR$^3$R$^4$ and —C(O)OR$^5$ and R$^1$ is hydrogen.

In one embodiment, the compound of Formula I is a compound as set forth in Table I below or a pharmaceutically acceptable salt thereof:

TABLE I

| Compound No. | R | L | R¹ |
|---|---|---|---|
| 1 | —C(O)CH₂CH₂N(CH₃)₂ | —C(O) | —CH₂CH₂N(CH₃)₂ |
| 2 | H | —C(O) | —CH₂CH₂N(CH₃)₂ |
| 3 | —C(O)CH₂CH₂N(CH₃)₂ | bond | H |
| 4 | —C(O)CH₂CH₂N(CH₃)₂ | bond | —CH₂N(CH₃)₂ |
| 5 | H | bond | —CH₂N(CH₃)₂ |
| 6 | —C(O)NHCH₂CH₂N(CH₃)₂ | —C(O) | H |
| 7 | —C(O)NHCH₂CH₂N(CH₃)₂ | —C(O)NH | —CH₂CH₂N(CH₃)₂ |
| 8 | H | —C(O)NH | —CH₂CH₂N(CH₃)₂ |
| 9 | —C(O)NHCH₂CH₂N(CH₃)₂ | —C(O)NH | H |
| 10 | —C(O)NHCH₂CH₂N(CH₃)₂ | —C(O) | —CH₃ |
| 11 | 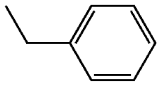 | —C(O) | —CH₂CH₂N(CH₃)₂ |
| 12 | —C(O)NHCH₂CH₂N(CH₃)₂ | —C(O) | —CH₂CH₂N(CH₃)₂ |
| 13 | —C(O)NHCH₂CH₂N(CH₃)₂ | —C(O)O | —CH₃ |
| 14 | —C(O)NHCH₂CH₂N(CH₃)₂ | —C(O)O | —CH₂CH₂N(CH₃)₂ |
| 15 | H | —C(O)O | —CH₂CH₂N(CH₃)₂ |
| 16 | —C(O)CH₃ | —C(O)NH | —CH₂CH₂N(CH₃)₂ |
| 17 | —C(O)CH₃ | —C(O)NH | H |
| 18 | —C(O)CH₃ | —C(O)NH | —CH₃ |
| 19 | —C(O)OCH₃ | —C(O)NH | —CH₂CH₂N(CH₃)₂ |
| 20 | —C(O)OCH₃ | —C(O)NH | H |
| 21 | —C(O)NHCH₂CH₂N(CH₃)₂ | —C(O)NH | 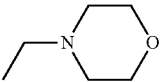 |
| 22 | H | —C(O)NH | 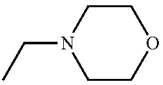 |
| 23 | —C(0)NHCH₂CH₂N(CH₃)₂ | —C(O)NH | 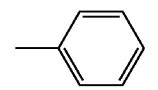 |
| 24 | —C(O)NHCH₂CH₂N(CH₃)₂ | —C(O) | 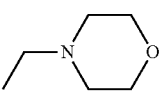 |
| 25 | H | —C(O) | 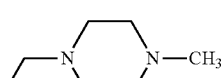 |
| 26 | —C(O)NHCH₂CH₂N(CH₃)₂ | —C(O) | 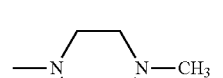 |
| 27 | C(O)NHCH₂CH₂N(CH₃)₂ | —C(O)O | 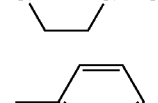 |
| 28 | —C(O)NHCH₃ | —C(O) | 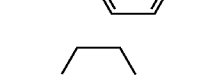 |
| 29 | H | —C(O) | 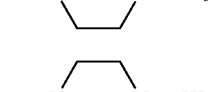 |
| 30 | 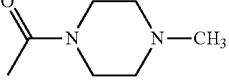 | —C(O)NH | —CH₂CH₂N(CH₃)₂ |
| 31 | —C(O)CH₃, | —C(O)O | —CH₃ |

TABLE I-continued

| Compound No. | R | L | R¹ |
|---|---|---|---|
| 32 | O=C-N(piperazine)N—CH₃ | —C(O)O— | —CH₂CH₃ |
| 33 | —C(O)CH₃ | —P(O)(OH)—O— | H |
| 34 | —C(O)CH₃ | —P(O)(OCH₃)—O— | —CH₂CH₂N(CH₃)₂ |
| 35 | H | —P(O)(OH)—O— | H |
| 36 | H | —P(O)(OCH₃)—O— | —CH₃ |
| 37 | —C(O)NHCH₂CH₂N(CH₃)₂ | —P(O)(OCH₃)—O— | —CH₃ |
| 38 | H | —C(O)NH— | —CH₃ |
| 39 | H | —C(O)O— | —CH₂CH₃ |
| 40 | H | —C(O)— | —N(piperazine)N—CH₃ |
| 41 | O=C-N(piperazine)N—CH₃ | —P(O)(OCH₃)—O— | —CH₃ |

In one of its composition aspects, this invention is directed to a pharmaceutical composition comprising a pharmaceutically acceptable excipient and a therapeutically effective amount of a compound of Formula I or Table I above.

In one of its method aspects, this invention is directed to a method for treating addiction in a patient which method comprises administering to the patient a pharmaceutical composition comprising a pharmaceutically acceptable excipient and a therapeutically effective amount of a compound of Formula I or Table I above.

In another of its method aspects, this invention is directed to a method for treating pain, addition and/or stress in a patient which method comprises administering to the patient a pharmaceutical composition comprising a pharmaceutically acceptable excipient and a therapeutically effective amount of a compound of Formula I or Table I above.

DETAILED DESCRIPTION

This invention is directed to noribogaine prodrugs, pharmaceutical compositions of such prodrugs and methods for their use. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of such excipients.

1. DEFINITIONS

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to compositions comprising noribogaine and an excipient to facilitate transport across the blood brain barrier.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH₃—), ethyl (CH₃CH₂—), n-propyl (CH₃CH₂CH₂—), isopropyl ((CH₃)₂CH—), n-butyl (CH₃CH₂CH₂CH₂—), isobutyl ((CH₃)₂CHCH₂—), sec-butyl ((CH₃)(CH₃CH₂)CH—), t-butyl ((CH₃)₃C—), n-pentyl (CH₃CH₂CH₂CH₂CH₂—), and neopentyl ((CH₃)₃CCH₂—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH₂C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{17}C(O)$alkyl, —$NR^{17}C(O)$substituted alkyl, —$NR^{17}C(O)$cycloalkyl, —$NR^{17}C(O)$substituted cycloalkyl, —$NR^{17}C(O)$cycloalkenyl, —$NR^{17}C(O)$substituted cycloalkenyl, —$NR^{17}C(O)$alkenyl, —$NR^{17}C(O)$substituted alkenyl, —$NR^{17}C(O)$alkynyl, —$NR^{17}C(O)$substituted alkynyl, —$NR^{17}C(O)$aryl, —$NR^{17}C(O)$substituted aryl, —$NR^{17}C(O)$heteroaryl, —$NR^{17}C(O)$substituted heteroaryl, —$NR^{17}C(O)$heterocyclic, and —$NR^{17}C(O)$substituted heterocyclic wherein $R^{17}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{18}R^{19}$ where $R^{18}$ and $R^{19}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{18}$ and $R^{19}$ are optionally joined, together with the nitrogen bound thereto to form a heterocyclic or substituted heterocyclic group, provided that $R^{18}$ and $R^{19}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{18}$ is hydrogen and $R^{19}$ is alkyl, the substituted amino group is sometimes referred to herein as alkylamino. When $R^{18}$ and $R^{19}$ are alkyl, the substituted amino group is sometimes referred to herein as dialkylamino. When referring to a monosubstituted amino, it is meant that either $R^{18}$ or $R^{19}$ is hydrogen but not both. When referring to a disubstituted amino, it is meant that neither $R^{18}$ nor $R^{19}$ are hydrogen.

"Aminocarbonyl" refers to the group —C(O)NR$^{20}$K$^{21}$ where $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{20}$R$^{21}$ where $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{17}$C(O)NR$^{20}$R$^{21}$ where $R^{17}$ is hydrogen or alkyl and $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{17}$C(S)NR$^{20}$R$^{21}$ where $R^{17}$ is hydrogen or alkyl and $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{20}$R$^{21}$ where $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{20}$R$^{21}$ where $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{20}$R$^{21}$ where $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{17}$—SO$_2$NR$^{20}$R$^{21}$ where $R^{17}$ is hydrogen or alkyl and $R^{20}$ and $R^{21}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{22}$)NR$^{20}$R$^{21}$ where $R^{20}$, $R^{21}$, and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{20}$ and $R^{21}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)β-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —$NR^{17}$—C(O)O-alkyl, —$NR^{17}$—C(O)O-substituted alkyl, —$NR^{17}$—C(O)O-alkenyl, —$NR^{17}$—C(O)O-substituted alkenyl, —$NR^{17}$—C(O)O-alkynyl, —$NR^{17}$—C(O)O-substituted alkynyl, —$NR^{17}$—C(O)O-aryl, —$NR^{17}$—C(O)O-substituted aryl, —$NR^{17}$—C(O)O-cycloalkyl, —$NR^{17}$—C(O)O-substituted cycloalkyl, —$NR^{17}$—C(O)O-cycloalkenyl, —$NR^{17}$—C(O)O-substituted cycloalkenyl, —$NR^{17}$—C(O)O-heteroaryl, —$NR^{17}$—C(O)O-substituted heteroaryl, —$NR^{17}$—C(O)O-heterocyclic, and —$NR^{17}$—C(O)O-substituted heterocyclic wherein $R^{17}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2]octanyl, norbornyl, and spirobicyclo groups such as spiro[4.5]dec-8-yl:

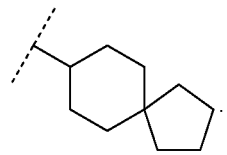

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{23}$C(=NR$^{23}$)N(R$^{23}$)$_2$ where each R$^{23}$ is independently selected from the group consisting of hydrogen, alkyl, substituted alkyl, aryl, substituted aryl, heteroaryl, substituted heteroaryl, heterocyclic, and substituted heterocyclic and two R$^{23}$ groups attached to a common guanidino nitrogen atom are optionally joined together with the nitrogen bound thereto to form a heterocyclic or substituted heterocyclic group, provided that at least one R$^{23}$ is not hydrogen, and wherein said substituents are as defined herein.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Haloalkoxy" refers to alkoxy groups substituted with 1 to 5, 1 to 3, or 1 to 2 halo groups, wherein alkoxy and halo are as defined herein.

"Haloalkylthio" refers to alkylthio groups substituted with 1 to 5, 1 to 3, or 1 to 2 halo groups, wherein alkylthio and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, and/or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

"Substituted heterocyclic" or "substituted heterocloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Spiro ring systems" refers to bicyclic ring systems that have a single ring carbon atom common to both rings.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—. The term "alkylsulfonyl" refers to —SO$_2$-alkyl. The term "haloalkylsulfonyl" refers to —SO$_2$-haloalkyl where haloalkyl is defined herein. The term "(substituted sulfonyl)amino" refers to —NH(substituted sulfonyl), and the term "(substituted sulfonyl)aminocarbonyl" refers to —C(O)NH (substituted sulfonyl), wherein substituted sulfonyl is as defined herein.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Compound" or "compounds" as used herein is meant to include the stereoisomers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

As used herein, the term "noribogaine" refers to the compound:

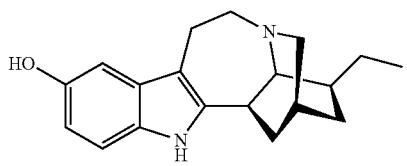

as well as its pharmaceutically acceptable salts thereof. Conventionally, noribogaine is prepared by demethylation of naturally occurring ibogaine:

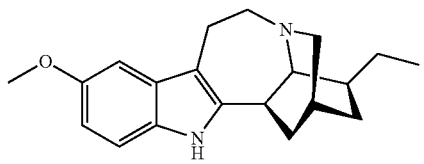

which is isolated from *Tabernanth iboga*, a shrub of West Africa. Demethylation may be accomplished by conventional techniques such as by reaction with boron tribromide/methylene chloride at room temperature followed by conventional purification. Methods for the synthesis and purification of noribogaine are disclosed in U.S. Patent Application No. 61/333,476, entitled Methods and Compositions for Preparing and Purifying Noribogaine, filed on May 11, 2010, which is hereby incorporated by reference in its entirety. This invention is not limited to any particular chemical form of noribogaine and the drug may be given to patients either as a free base or as a pharmaceutically acceptable addition salt.

As used herein, the term "pharmaceutically acceptable salt" refers to salts derived from organic or inorganic acids. Examples of such acids include, without limitation, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like.

As used herein, the term "therapeutically effective amount" refers to the amount of a composition of this invention that is sufficient to effect treatment, as defined herein, when administered to a subject in need of such treatment. The therapeutically effective amount will vary depending upon the subject and condition being treated, the weight and age of the subject, the severity of the condition, the particular composition or excipient chosen, the dosing regimen to be followed, timing of administration, the manner of administration and the like, all of which can be determined readily by one of ordinary skill in the art.

As used herein, the term "treatment" or "treating" means any treatment of a disease or condition in a patient, including:
  preventing or protecting against the disease or condition, that is, causing the clinical symptoms not to develop, for example, in a subject at risk of suffering from such a disease or condition, thereby substantially averting onset of the disease or condition;
  inhibiting the disease or condition, that is, arresting or suppressing the development of clinical symptoms; and/or
  relieving the disease or condition that is, causing the regression of clinical symptoms.

As used herein, the term "pain" refers to all types of pain, including neuropathic and nociceptive pain. It is also contemplated that the compositions disclosed herein can be used to treat other types of pain such as phantom pain which is the sensation of pain from a limb or organ that has been lost or from which a person no longer receives physical signals, and is an experience almost universally reported by amputees and quadriplegics.

As used herein, the term "addiction" refers to a persistent behavioral pattern marked by physical and/or psychological dependency to a substance, particularly drugs such as narcotics, stimulants, and sedatives, including but not limited to heroin, cocaine, alcohol, nicotine, caffeine, amphetamine, desoxyephedrine, methadone and combinations thereof. As used herein, the "treatment of addiction in a patient" refers to reducing the withdrawal symptoms associated with drug dependency as well as alleviating drug cravings in addicts. Such symptoms include nausea, vomiting, anxiety, abdominal cramps, muscle pain, chills and headache.

As used herein, the terms "blood-brain barrier" or "BBB" refer to the barrier between the peripheral circulation and the brain and spinal cord which is formed by tight junctions within the brain capillary endothelial plasma membranes, creating an extremely tight barrier that restricts the transport of molecules into the brain. The blood-brain barrier within the brain, the blood-spinal cord barrier within the spinal cord, and the blood-retinal barrier within the retina, are contiguous capillary barriers within the central nervous system (CNS), and are collectively referred to herein as the blood-brain barrier or BBB.

As used herein, the term "cleavable linking group" refers to a linking group that can be attached to noribogaine at any possible position. Preferably, the linker is biocompatible (i.e. does not produce undesired side effects or have an intolerable toxicity), is readily cleaved in the body (preferably in the brain), and does not inhibit or alter the desired physiological effect of noribogaine. Specifically, the linking group is preferably sufficiently stable in the circulatory system (serum or blood), but is cleaved to release the noribogaine upon entry into the brain. Suitable biocompatible, cleavable linking groups comprise from 1 to 20 atoms selected from carbon, nitrogen, oxygen, sulfur, and phosphorus, and are, in general, susceptible to cleavage conditions or agents in the brain (i.e. pH, redox potential or the presence of degradative molecules such as enzymes). The biocompatible, cleavable linking group can be an ester-based cleavable linking group (—C(O)O— or —OC(O)—), an amide-based cleavable linking group (—C(O)NR$^9$— or —NR$^9$C(O)—), or a phosphate-based cleavable linking group (—P(O)(OR$^9$)—O—, —O—P(S)(OR$^9$)—O—, —O—P(S)(SR)—O—, —S—P(O)(OR$^9$)—O—, —O—P(O)(OR$^9$)—S—, —S—P(O)(OR$^9$)—S—, —O—P(S)(OR$^9$)—S—, —S—P(S)(OR$^9$)—O—, —O—P(O)(R$^9$)—O—, —O—P(S)(R$^9$)—O—, —S—P(O)(R$^9$)—O—, —S—P(S)(R$^9$)—O—, —S—P(O)(R$^9$)—S—, or —O—P(S)(R$^9$)—S—) where R$^9$ can be hydrogen or alkyl.

As used herein, the term "saccharide" or "monosaccharide" refers to a saccharide or derivative thereof, having at least 6 carbon atoms (which may be linear, branched or cyclic) with an oxygen, nitrogen or sulfur atom bonded to each carbon atom. The term "oligosaccharides" includes oligosaccharides containing from about 2-9 monosaccharide units. Specific monosaccharides include C$_5$ and above (preferably C$_5$-C$_8$) saccharides such as ethritol, zylitol, galactose, lactose, xylose, dulcitol, myo-insoitol, fructose, mannitol, sorbitol, glucose, arabinose, arabinose, celloboise, maltose, raffinose, rhamnose, melibiose, ribose, adonitol, arabitol, arabitol, fucose, lyxose, lyxose, lyxose, glucosamine, mannosamine, and galactosamine; di- and trisaccharides include saccharides having two or three monosaccharide units.

As used herein, the term "patient" refers to mammals and includes humans and non-human mammals.

2. COMPOUNDS

Accordingly, in one embodiment, this invention is directed to compounds which are represented by Formula I below:

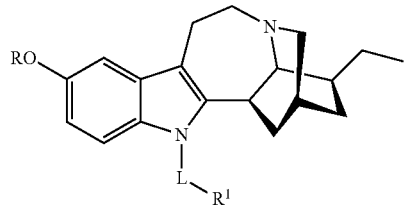

wherein
R is selected from the group consisting of hydrogen, a hydrolysable group selected from the group consisting of —C(O)R$^2$, —C(O)NR$^3$R$^4$ and —C(O)OR$^5$, where R$^2$ is selected from the group consisting of hydrogen, alkyl, substituted alkyl, alkenyl, substituted alkenyl, alkynyl and substituted alkynyl, R$^3$ and R$^4$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, R$^5$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that R is not a saccharide or an oligosaccharide;

L is selected from the group consisting of a covalent bond and a cleavable linker group;

R$^1$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, provided that R$^1$ is not a saccharide or an oligosaccharide;

or pharmaceutically acceptable salts thereof,
provided that when L is a covalent bond and R$^1$ is hydrogen, then R is selected from the group consisting of —C(O)NR$^3$R$^4$ and —C(O)OR$^5$; and further provided that when R is hydrogen or —C(O)R$^2$ and L is a covalent bond, then R$^1$ is not hydrogen.

In one embodiment, R is hydrogen and L is a cleavable group.

In one embodiment, L is a suitable biocompatible, cleavable linking group. Suitable biocompatible, cleavable linking groups comprise a covalent bond and a linking group having from 1 to 20 atoms selected from carbon, nitrogen, oxygen, sulfur, and phosphorus, and are, in general, susceptible to cleavage conditions or agents in the brain (i.e. pH, redox potential or the presence of degradative molecules such as enzymes, e.g., proteases, lipases, etc.). Generally, the cleavage conditions or agents should be more prevalent or found at higher levels or activities in the brain than in serum or blood. Examples of degradative agents include: redox agents which are selected for particular substrates or which have no substrate specificity, including, e.g., oxidative or reductive enzymes or reductive agents such as esterases; enzymes that can hydrolyze or degrade an acid cleavable linking group by acting as a general acid, peptidases (which can be substrate specific), and phosphatases.

In general, the suitability of a candidate cleavable linking group can be evaluated by testing the ability of a cleaving agent (or condition) to cleave the linking group. It will also be desirable to also test the linking group for the ability to resist cleavage in the serum, blood or when in contact with other non-target tissue. Thus one can determine the relative susceptibility to cleavage between a first and a second condition, where the first is indicative of cleavage in the brain and the second is indicative of cleavage in serum, blood or other non-target tissue. Such evaluations can be carried out in cell-free systems, in cells, in cell culture, in organ or tissue culture, or in whole animals. In preferred embodiments, the cleavable linking group is cleaved at least 2, 4, 10 or 100 times faster in the brain as compared to serum, blood or other non-target tissue.

In one embodiment, the linking group is an ester-based linking group. In another embodiment, the linking group is an amide-based linking group. In yet another embodiment, the linking group is a phosphate-based linking group. In another embodiment of the compounds of this invention, L is a covalent bond.

In one embodiment, L is —C(O)—. In another embodiment, L is —C(O)O—. In still another embodiment, L is —C(O)NR—, where R is hydrogen or alkyl.

In one embodiment, L is selected from the group consisting of —P(O)(OR$^9$)—O—, —O—P(S)(OR$^9$)—O—, —O—P(S)(SR$^9$)—O—, —S—P(O)(OR$^9$)—O—, —O—P(O)(OR$^9$)—S—, —S—P(O)(OR$^9$)—S—, —O—P(S)(OR$^9$)—S—, —S—P(S)(OR$^9$)—O—, —O—P(O)(R$^9$)—O—, —O—P(S)(R$^9$)—O—, —S—P(O)(R$^9$)—O—, —S—P(S)(R$^9$)—O—, —S—P(O)(R$^9$)—S—, and —O—P(S)(R$^9$)—S—, where R$^9$ is hydrogen or alkyl.

In one embodiment, R is hydrogen, L is a covalent bond or —C(O)—, and R$^1$ is substituted alkyl. Preferably R$^1$ is alkyl substituted with —NR$^6$R$^7$ where R$^6$ and R$^7$ are independently selected from the group consisting of hydrogen, alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

In one embodiment, R is selected from the group consisting of —C(O)NR$^3$R$^4$ and —C(O)OR$^5$ and R$^1$ is hydrogen.

In one embodiment, the compound of Formula I is a compound as set forth in Table I below or a pharmaceutically acceptable salt thereof:

TABLE I

| Compound No. | R | L | R$^1$ |
|---|---|---|---|
| 1 | —C(O)CH$_2$CH$_2$N(CH$_3$)$_2$ | —C(O) | —CH$_2$CH$_2$N(CH$_3$)$_2$ |
| 2 | H | —C(O) | —CH$_2$CH$_2$N(CH$_3$)$_2$ |
| 3 | —C(O)CH$_2$CH$_2$N(CH$_3$)$_2$ | bond | H |
| 4 | —C(O)CH$_2$CH$_2$N(CH$_3$)$_2$ | bond | —CH$_2$N(CH$_3$)$_2$ |
| 5 | H | bond | —CH$_2$N(CH$_3$)$_2$ |
| 6 | —C(O)NHCH$_2$CH$_2$N(CH$_3$)$_2$ | —C(O) | H |
| 7 | —C(O)NHCH$_2$CH$_2$N(CH$_3$)$_2$ | —C(O)NH | —CH$_2$CH$_2$N(CH$_3$)$_2$ |
| 8 | H | —C(O)NH | —CH$_2$CH$_2$N(CH$_3$)$_2$ |
| 9 | —C(O)NHCH$_2$CH$_2$N(CH$_3$)$_2$ | —C(O)NH | H |
| 10 | —C(O)NHCH$_2$CH$_2$N(CH$_3$)$_2$ | —C(O) | —CH$_3$ |
| 11 | 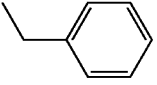 | —C(O) | —CH$_2$CH$_2$N(CH$_3$)$_2$ |
| 12 | —C(O)NHCH$_2$CH$_2$N(CH$_3$)$_2$ | —C(O) | —CH$_2$CH$_2$N(CH$_3$)$_2$ |
| 13 | —C(O)NHCH$_2$CH$_2$N(CH$_3$)$_2$ | —C(O)O | —CH$_3$ |
| 14 | —C(O)NHCH$_2$CH$_2$N(CH$_3$)$_2$ | —C(O)O | —CH$_2$CH$_2$N(CH$_3$)$_2$ |
| 15 | H | —C(O)O | —CH$_2$CH$_2$N(CH$_3$)$_2$ |
| 16 | —C(O)CH$_3$, | —C(O)NH | —CH$_2$CH$_2$N(CH$_3$)$_2$ |
| 17 | —C(O)CH$_3$, | —C(O)NH | H |
| 18 | —C(O)CH$_3$, | —C(O)NH | —CH$_3$ |
| 19 | —C(O)OCH$_3$, | —C(O)NH | —CH$_2$CH$_2$N(CH$_3$)$_2$ |
| 20 | —C(O)OCH$_3$, | —C(O)NH | H |
| 21 | —C(O)NHCH$_2$CH$_2$N(CH$_3$)$_2$ | —C(O)NH | 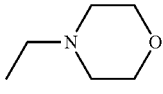 |
| 22 | H | —C(O)NH | 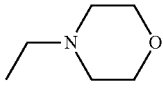 |
| 23 | —C(O)NHCH$_2$CH$_2$N(CH$_3$)$_2$ | —C(O)NH | 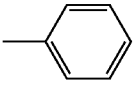 |
| 24 | —C(O)NHCH$_2$CH$_2$N(CH$_3$)$_2$ | —C(O) | 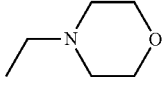 |
| 25 | H | —C(O) | 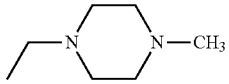 |

TABLE I-continued

| Compound No. | R | L | R¹ |
|---|---|---|---|
| 26 | —C(O)NHCH$_2$CH$_2$N(CH$_3$)$_2$ | —C(O) | 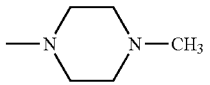 |
| 27 | —C(O)NHCH$_2$CH$_2$N(CH$_3$)$_2$ | —C(O)O | 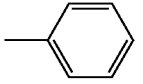 |
| 28 | —C(O)NHCH$_3$ | —C(O) | 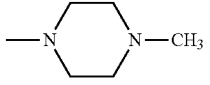 |
| 29 | H | —C(O) | 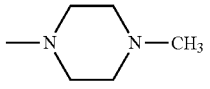 |
| 30 |  | —C(O)NH | —CH$_2$CH$_2$N(CH$_3$)$_2$ |
| 31 | —C(O)CH$_3$, | —C(O)O | —CH$_3$ |
| 32 |  | —C(O)O | —CH$_2$CH$_3$ |
| 33 | —C(O)CH$_3$, | —P(O)(OH)—O— | H |
| 34 | —C(O)CH$_3$, | —P(O)(OCH$_3$)—O— | —CH$_2$CH$_2$N(CH$_3$)$_2$ |
| 35 | H | —P(O)(OH)—O— | H |
| 36 | H | —P(O)(OCH$_3$)—O— | —CH$_3$ |
| 37 | —C(O)NHCH$_2$CH$_2$N(CH$_3$)$_2$ | —P(O)(OCH$_3$)—O— | —CH$_3$ |
| 38 | H | —C(O)NH | —CH$_3$ |
| 39 | H | —C(O)O | —CH$_2$CH$_3$ |
| 40 | H | —C(O) | 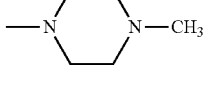 |
| 41 | 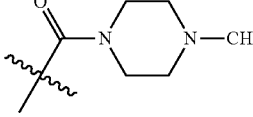 | —P(O)(OCH$_3$)—O— | —CH3 |

3. METHODS OF USE

Compounds of this invention are contemplated to be useful in treating pain and/or addiction as an active ingredient or a prodrug. In some embodiments, the compounds of this invention are prodrugs whose R and/or -L-R¹ groups are cleaved in vivo to produce noribogaine. In a preferred embodiment, the compound is at least 2, 5 or 10 times more stable in serum plasma than in the central nervous system, such as the brain. In a more preferred embodiment, the prodrugs have improved BBB penetration property as compared with noribogaine, for example, the compounds of this invention have at least 20%, 50% or 100% more BBB penetration ability than noribogaine.

Treatment of Pain

In one of its method aspects, the present invention is directed to a method for treating a pain in a patient which method comprises administering to said patient a compound of this invention or a pharmaceutically acceptable salt thereof or a pharmaceutical composition comprising a compound of this invention and a pharmaceutically acceptable excipient. The pain can be any type of pain including, but not limited to neuropathic or nociceptive pain, and various types thereof including somatic, visceral and phantom pain.

Treatment of Addiction

In another of its method aspects, the present invention is directed to a method for treating addiction in a patient which method comprises administering to said patient a compound of this invention or a pharmaceutically acceptable salt thereof or a composition comprising a compound of this invention and a pharmaceutically acceptable excipient.

In certain embodiments, the treatment of addiction in a patient comprises alleviating the symptoms associated with withdrawal from drug dependency. Such symptoms include nausea, vomiting, anxiety, abdominal cramps, muscle pain, chills and headache. In addition, it is contemplated that treatment with a compound of this invention decreases the drug cravings normally experienced by addicts after cessation of the self administration of the abused substance. It is contemplated that the compositions disclosed herein are especially useful in the treatment of addiction to narcotics such as heroin and methadone. However, it is also useful in treating patients addicted to cocaine, alcohol, amphetamines and combinations of these drugs.

The invention is also directed to a method for treating drug addiction (involving drug dependency or drug abuse) during withdrawal therapy by administering a compound of this invention to a patient at a dosage sufficient to reduce or eliminate one or more symptoms associated with withdrawal. Such symptoms include nausea, vomiting, anxiety, abdominal cramps, muscle pain, chills and headache. In addition, treatment with a compound of this invention is contemplated to decrease the drug cravings normally experienced by addicts after cessation of the self administration of the abused substance, for example, narcotics such as heroin and methadone. However, compounds of this invention are contemplated to be also useful in treating patients addicted to cocaine, alcohol, amphetamines and combinations of these drugs. Compounds of this invention may be administered to patients suffering from drug dependence or abuse in conjunction with an opioid antagonist such as naloxone, naltrexone or nalorphine, for example, at a concentration of between 0.15 mg and 0.5 mg for each mg of the compound of this invention administered.

Treatment of Stress

In another of its method aspects, the present invention is directed to a method for treating stress, such as post-traumatic stress disorder, in a patient in need of the treatment, which method comprises administering to said patient a compound of this invention or a pharmaceutically acceptable salt thereof or a composition comprising a compound of this invention and a pharmaceutically acceptable excipient.

Stress or anxiety refers to the consequence when a patient fails to respond appropriately to emotional or physical threats, which may be actual or imagined. Stress symptoms or conditions may be cognitive, emotional, physical or behavioral, including, but not limited to a state of alarm and adrenaline production, short-term resistance as a coping mechanism, exhaustion, irritability, muscular tension, inability to concentrate, poor judgment, a general negative outlook, excessive worrying, moodiness, irritability, agitation, inability to relax, feeling lonely, isolated or depressed, aches and pains, diarrhea or constipation, nausea, dizziness, chest pain, headache, rapid heartbeat, eating too much or not enough, sleeping too much or not enough, social withdrawal, procrastination or neglect of responsibilities, increased alcohol, nicotine or drug consumption, and nervous habits such as pacing about or nail-biting. Stress can develop into a disabling disorder of excessive and irrational fears, such as obsessive-compulsive disorder, panic disorder, acute stress disorder and post traumatic stress disorder (PTSD).

PTSD is a severe stress disorder that can develop after exposure to an event which results in psychological trauma. Such events usually involve death of someone else, threat of death to oneself or to someone else, or trauma to the physical, sexual, or psychological integrity of one's own or someone else. PTSD may be an acute stress response or a long term stress response to such an event when it overwhelms one's ability to cope.

Symptoms of PTSD include some or all of the following: recurrent re-experiencing of the trauma, for example, intrusive, upsetting memories of the event, flashbacks of the traumatic events (acting or feeling like the event is happening again), recurring nightmares (either of the event or of other frightening things); feelings of intense distress and/or intense physical reactions when reminded of the trauma; avoidance to the point of having a phobia of places, people, and experiences that remind the sufferer of the trauma and a general numbing of emotional responsiveness; inability to remember important aspects of the trauma; and physical signs of hyper-arousal, including sleep problems, trouble concentrating, irritability, anger, poor concentration, blackouts or difficulty remembering things, increased tendency and reaction to being startled, and hypervigilance to threat. Other symptoms include anhedonia, lack of interest in activities that used to be enjoyed, emotional deadness, distancing oneself from people, and/or a sense of a limited future (for example, not being able to think about the future or make future plans, not believing one will live much longer), guilt, shame, self-blame, depression and hopelessness, suicidal thoughts and feelings, feeling alienated and alone, headaches, stomach problems, chest pain and substance abuse.

Combination Therapy

Compounds of this invention may be used alone or in combination with other compounds to treat pain, addiction and/or stress. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

In some embodiments, a compound of this invention can be used as an adjunct to conventional drug withdrawal therapy, specifically providing for the administration of a compound of this invention with one or more opioid antagonists.

4. COMPOSITIONS

In another aspect, this invention is also directed to pharmaceutical compositions comprising a pharmaceutically acceptable excipient and a compound of this invention or mixtures of one or more of such compounds.

Although compositions suitable for oral, intravenous or intraarterial delivery will probably be used most frequently, other routes that may be used include peroral, pulmonary, rectal, nasal, vaginal, lingual, intramuscular, intraperitoneal, intracutaneous and subcutaneous routes. In addition, it is contemplated that the composition can be administered transdermally in which drug is applied as part of a cream, gel, or patch (for examples of transdermal formulations, see U.S. Pat. Nos. 4,806,341; 5,149,538; and 4,626,539). Other dosage forms include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980). Intranasal administration is an effective method for delivering a therapeutic agent directly to the respiratory tract, where the therapeutic agent may be quickly absorbed.

The compositions are comprised of in general, a compound of this invention or a mixture thereof in combination with at least one pharmaceutically acceptable excipient. Acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

The amount of the compound in a formulation can vary within the full range employed by those skilled in the art. Typically, the formulation will contain, on a weight percent (wt %) basis, from about 0.01 to 99.99 wt % of a compound of this invention based on the total formulation, with the balance being one or more suitable pharmaceutical excipients. Preferably, the compound is present at a level of about 1 to 80 wt %. In a liquid composition, a compound of this invention should generally be present in such compositions at a concentration of between about 0.1 and 20 mg/ml. When either naloxone or naltrexone is combined with a compound of this invention, they should be present at 0.05 to 0.5 mg for each mg of the compound of this invention.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Generally, the compound of this invention is administered in an effective amount. It is contemplated that the dosage required for treating pain or addition, or a combination thereof may differ according to the condition(s) being treated, however, the dosing regimen can be readily determined by the attending clinician based on the desired treatment. It is contemplated that generally, the dosage of a compound of this invention administered to a patient may be from about 0.01 to about 1000 mg per kg of body weight per day (mg/kg/day), or from 0.05 to 500 mg/kg/day, preferably, from about 0.1 to about 100 mg/kg/day, more preferably from about 0.5 to 50 mg/kg/day. For example, for administration to a 70 kg person, the dosage range would preferably be about 35 to 700 mg per day.

In addition to the methods discussed above, the present invention is directed to a pharmaceutical composition, preferably in unit dose form, comprising a compound of this invention. When administered to a patient, one or more unit doses provide an amount of a compound of this invention effective to treat pain and/or addition.

The amount of the composition administered will depend on a number of factors, including but not limited to the desired final concentration of the compound, the pharmacokinetic and pharmacodynamic properties of the compound, the size, age, and physiological profile of the patient, and the like. The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

Determination of dosages is well within the empiric knowledge of persons skilled in the art; nonetheless, it can be appreciated that estimates of final dosages can be made by approximating the concentration of compound necessary to achieve a desired therapeutic activity, such as treatment of pain and/or addiction. Extrapolation to a specified mammalian dosage range, or more particularly a human dosage range is well within the skill of the practitioner.

In some embodiments, compositions are administered in one dosing of a single formulation and in other embodiments, compositions are administered in multiple dosing of a single formulation within a specified time period. In some embodiments, the time period is between about 3 hours to about 6 hours. In other embodiments, the time period is between about 6 hours and 12 hours. In additional embodiments, the time period is between about 12 hours and 24 hours. In yet further embodiments, the time period is between about 24 hours and 48 hours. The administration of separate formulations can be simultaneous or staged throughout a specified time period, such that all ingredients are administered within the specified time period.

5. SYNTHETIC METHODS

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Still further, some of the compounds defined herein include vinyl groups which can exist in cis, trans or a mixture of cis and trans forms. All combinations of these forms are within the scope of this invention.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4.sup.th Edition), and Larock's Comprehensive Organic Transformations (VCH Publishers Inc., 1989).

Compounds of Formula I can be readily prepared from noribogaine by methods known to one of skill in the art. A skilled artisan would appreciate that the reactivity of the hydroxy group and the indole nitrogen is different so that selectivity can be achieved by selecting suitable reagents and suitable reaction conditions for one of them to react but leaving the other intact to form the desired product. For example, the hydroxy group is expected to selectively react with an acid $R^2C(O)OH$ in the presence of triphenylphosphine ($Ph_3P$) and diethyl azodicarboxylate (DEAD) to give compound 1-1 and 1-3. Thus, as shown in Scheme 1, noribogaine can react with LG-R where LG is a leaving group such as hydroxy, alkoxy, halo, etc., to give compound 1-1, which may further react with LG-L-$R^1$ to form compound 1-2. In other embodiments (i.e. when R is H), the phenol is protected by reaction with a suitable protecting group, PG-LG, where LG is a leaving group such as defined above, such that the indole nitrogen is derivatized with L-$R^1$. Suitable protecting groups are well known in the art (see T. W. Greene, P. G. M. Wuts, Protective Groups in Organic Synthesis, 4$^{th}$ Edition, Wiley-Interscience, New York, 2006). In another alternative embodiment (i.e. when L is a bond and $R^1$ is H), the indole nitrogen is protected with a suitable protecting group, PG (see Greene et al., supra), such phenol that is derivatized with R.

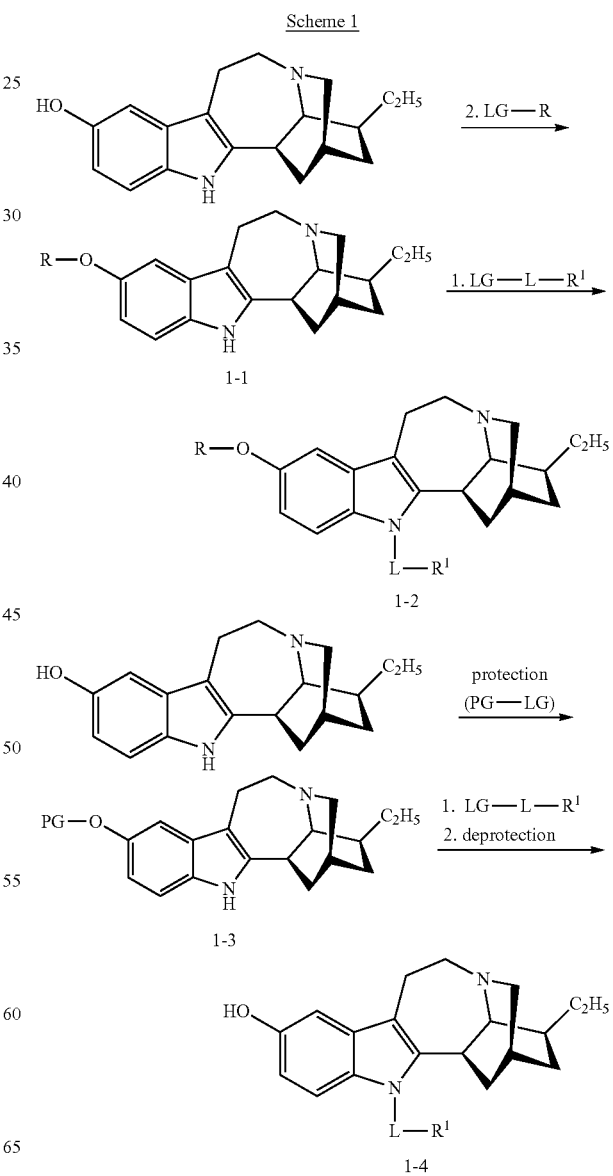

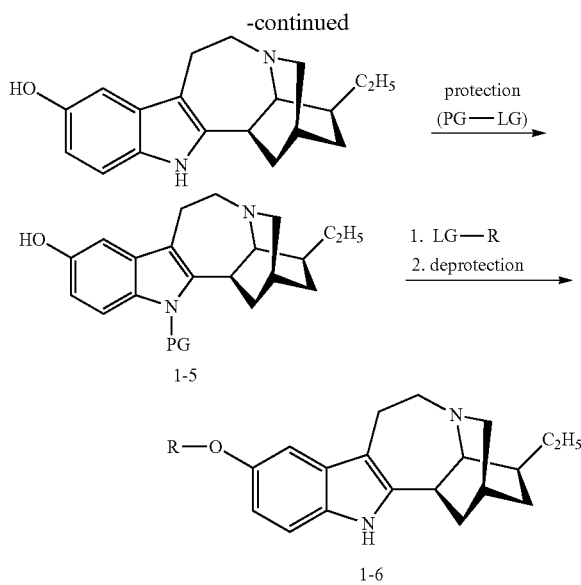

Alternatively, as shown in Scheme 2, compounds of this invention wherein L-R¹ is not hydrogen may be prepared by reacting ibogaine with LG-L-R¹ to give compound 2-1. Compound 2-1 can be demethylated by methods known in the art, such as reaction with boron tribromide/methylene chloride at room temperature to give compound 1-4, which may further react with LG-R to give compound 1-2.

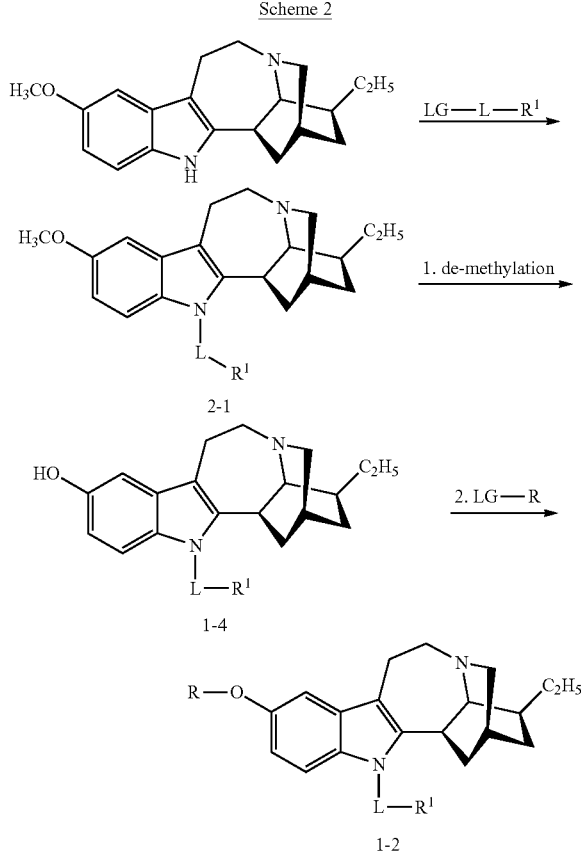

EXAMPLES

The present invention is further defined by reference to the following examples. It will be apparent to those skilled in the art that many modifications, both to materials and methods, may be practiced without departing from the scope of the current invention.

TABLE 2

List of abbreviations and acronyms.

| Abbreviation | Meaning |
|---|---|
| °C. | Degree Celcius |
| Ac | Acetyl |
| bs | Broad singlet |
| ca. | Approximately |
| CDI | N,N'-Carbonyl diimidazole |
| d | Doublet |
| dd | Doublet of doublets |
| DEAD | Diethyl azodicarboxylate |
| DIPEA | N,N-Diisopropylethylamine |
| DMAP | 4-Dimethylaminopyridine |
| DMF | Dimethylformamide |
| Et | Ethyl |
| g | Gram |
| h | Hour |
| HPLC | High-performance liquid chromatography |
| Hz | Hertz |
| i.v. | Intravenous |
| Kg | Kilogram |
| M | Molar |
| m | Multiplet |
| M+1 | Mass peak |
| Me | Methyl |
| mg | Milligram |
| MHz | Megahertz |
| min | Minute |
| mL | Milliliter |
| mmol | Millimole |
| MS | Mass spectrometry |
| N | Normal |
| NaHDMS | Sodium hexamethyldisilazane |
| NMR | Nuclear magnetic resonance |
| Ph | Phenyl |
| q | Quartet |
| q.s. | Sufficient amount |
| r.t./rt | Room temperature |
| s | Singlet |
| t | Triplet |
| TBAF | Tetra-n-butylammonium fluoride |
| TBS | tert-Butyldimethylsilyl |
| TBSCl | tert-Butyldimethylsilyl chloride |
| td | Triplet of doublets |
| THF | Tetrahydrofuran |
| TLC | Thin layer chromatography |
| v/v | Volume/volume |
| wt % | Weight percent |
| δ | Chemical shift |
| μL | Microliter |

Compounds of the invention can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene, P. G. M. Wuts, Protective Groups in Organic Synthesis, 4$^{th}$ Edition, Wiley-Interscience, New York, 2006, and references cited therein. The starting materials for the following reactions are generally known compounds or can be prepared by known procedures or obvious modifications thereof. For example, many of the starting materials are available from commercial suppliers such as Aldrich® Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Example 1

Preparation of Compound 1

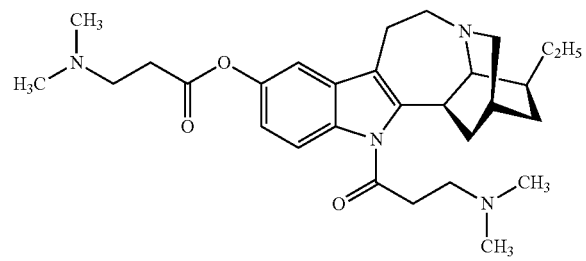

Compound 1 may be prepared by reacting noribogaine with at least two equivalents of $(CH_3)_2NCH_2CH_2C(O)Cl$ in the presence of a base in a suitable solvent. In one embodiment, the reaction is conducted in a polar solvent. Upon reaction completion, compound 1 can be recovered by conventional techniques such as neutralization, extraction, precipitation, chromatography, filtration and the like; or, alternatively, used without purification and/or isolation.

Example 2

Preparation of Compound 2

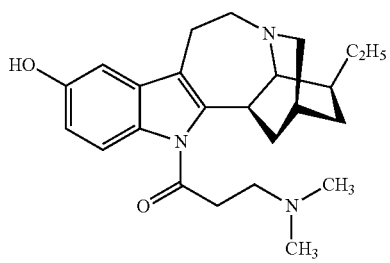

Compound 2 may prepared by reacting noribogaine with at least one equivalent of $(CH_3)_2NCH_2CH_2C(O)Cl$ in the presence of a base in a suitable solvent to give an intermediate product. In one embodiment, the reaction is conducted in a polar solvent. The intermediate product can be demethylated by reaction with boron tribromide/methylene chloride at room temperature to give compound 2, Upon reaction completion, compound 2 can be recovered by conventional techniques such as neutralization, extraction, precipitation, chromatography, filtration and the like; or, alternatively, used without purification and/or isolation.

Example 3

Preparation of Compound 3

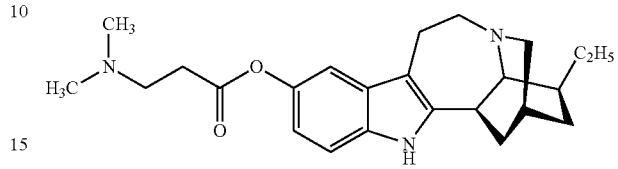

Compound 3 may prepared by reacting noribogaine with one equivalent of $(CH_3)_2NCH_2CH_2C(O)Cl$ in the presence of a base, such as pyridine, in a suitable solvent, or with one equivalent of $(CH_3)_2NCH_2CH_2C(O)OH$ in the presence of triphenylphosphine ($Ph_3P$) and diethyl azodicarboxylate (DEAD). In one embodiment, the reaction is conducted in a polar solvent. Upon reaction rational completion, compound 3 can be recovered by conventional techniques such as neutralization, extraction, precipitation, chromatography, filtration and the like; or, alternatively, used without purification and/or isolation.

Example 4

Preparation of Compound 8

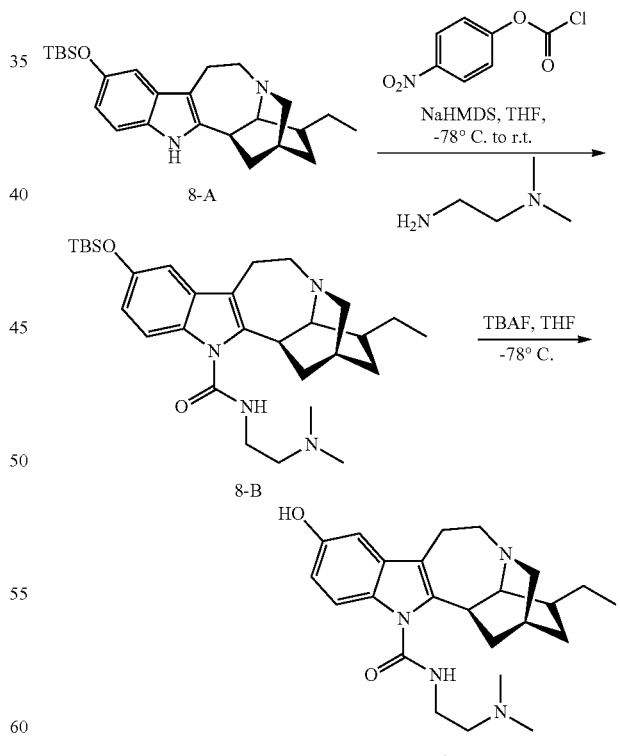

a) Preparation of TBS-Noribogaine 8-A

A suspension of noribogaine hydrochloride (852 mg, 2.56 mmol), TBS-Cl (444 mg, 2.94 mmol) and imidazole (227 mg, 3.33 mmol) in DMF (6 mL) was stirred at room temperature for 20 h. The resulting clear solution was diluted with 10%

2-propanol/dichloromethane and washed with water and brine. The aqueous phase was extracted with EtOAc. The combined organic layers were concentrated and purified by column chromatography (EtOAc/Hexanes, v/v, 2/1) to give compound 8-A (911 mg, 87%) as a white solid.

MS calculated for ($C_{25}H_{38}N_2OSi$): 410; MS found, (M+1): 411.

b) Preparation of Compound 8-B

NaHMDS (0.75 mL, 1.0 M solution in THF) was added into a solution of TBS-noribogaine 8-A (205 mg, 0.5 mmol) in THF (10 mL) at −78° C. The resulting solution was stirred for 10 min at −78° C. then a solution of 4-nitrophenyl chloroformate (182 mg, 0.9 mmol) in THF (8 mL, pre-cooled to −78° C.) was added quickly. The reaction mixture was allow to warm to room temperature and stir for 1 hour, followed by the addition of N,N-dimethylethylenediamine (0.22 mL, 2.0 mmol). After stirring at room temperature for an additional hour, the reaction mixture was diluted with 10% 2-propanol/dichloromethane and washed with water and brine. The aqueous phase was extracted with EtOAc. The combined organic layers were concentrated and purified by column chromatography (EtOAc/Hexanes, v/v, 2/1 to 99:1 EtOAc:triethylamine). The desired product compound 8-B (138 mg, 53%) was obtained as white solid.

MS calculated for ($C_{30}H_{48}N_4O_2Si$): 524; MS found, (M+1): 525.

c) Preparation of Compound 8

TBAF (0.68 mL, 1.0 M solution in THF, 0.68 mmol) was added to a solution of compound 8-B (178 mg, 0.34 mmol) in THF (12 mL) at −78° C. The resulting solution was stirred for 40 min at −78° C. before it was quenched by addition of 1N aqueous HCl (2 mL). The reaction mixture was allowed to warm to room temperature and was concentrated. The residue was purified by Preparative-HPLC to give compound 8 as the hydrochloride salt (110 mg, HCl salt, 72%) as a white solid.

MS calculated for ($C_{24}H_{34}N_4O_2$): 410; MS found, (M+1): 411. $^1$H NMR (300 MHz, $CD_3OD$) δ 8.20 (bs, 1H), 7.49 (d, 1H), 6.87 (s, 1H), 6.80 (d, 1H), 3.50-3.92 (m, 6H), 3.36-3.58 (m, 4H), 3.00-3.36 (m, 2H), 2.80-3.00 (m, 6H), 2.50 (td, 1H), 1.85-2.20 (m, 3H), 1.48-1.82 (m, 3H), 1.22-1.46 (m, 1H), 1.04 (t, 3H).

Example 5

Preparation of Compound 15

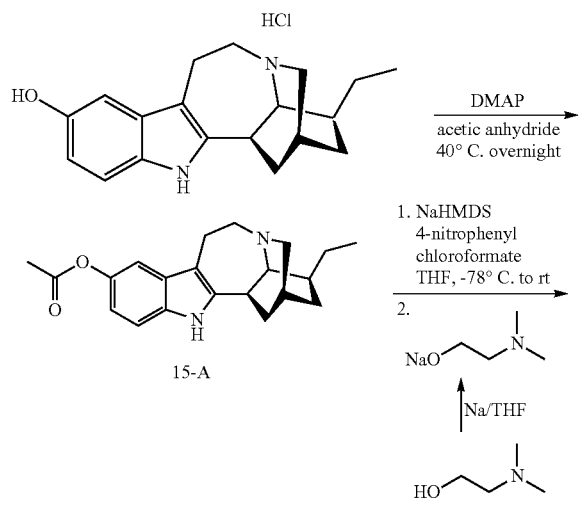

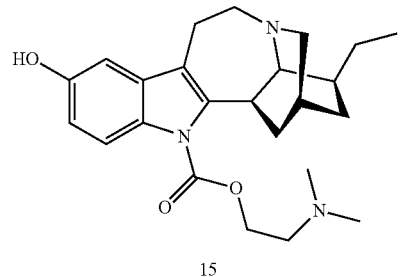

a) Preparation of Noribogaine Acetate 15-A

A mixture of noribogaine (300 mg, 0.9 mmol) and DMAP (10 mg, 0.09 mmol) in acetic anhydride (6 mL) was heated at 40° C. for 16 h. The acetic anhydride was co-evaporated with toluene at 40° C. under reduced pressure. The residue was dissolved in ethyl acetate (100 mL), and the resulting solution was stirred with saturated $NaHCO_3$ solution (50 mL) at rt for 2 h. The organic phase was separated and concentrated under reduced pressure. The crude product was purified by chromatography on silica gel (ethyl acetate/hexane:=1/2) to give compound 15-A (280 mg, 90%) as white solid.

MS calculated for ($C_{21}H_{26}N_2O_2$)$^+$: 338; MS found, (M+1): 339. $^1$H NMR (300 MHz, $CD_3OD$) δ 7.18 (d, J=8.4 Hz, 1H), 7.06 (d, J=2.4 Hz, 1H), 6.7 (dd, J=8.4 Hz, J=2.4 Hz, 1H), 3.38 (m, 1H), 3.1 (m, 4H), 2.95 (m, 2H), 2.65 (m, 1H), 2.27 (s, 3H), 2.14 (m, 1H), 1.88 (m, 2H), 1.64-1.45 (m, 4H), 1.23 (m, 1H), 0.94 (t, J=7.5 Hz, 3H).

b) Preparation of Compound 15

To a solution of N,N-dimethylethanolamine (0.6 mL, 6 mmol) in THF (1.4 mL) was added sodium (46 mg, 2 mmol) at rt. The reaction mixture was stirred at rt until the sodium disappeared. The resulting solution of sodium N,N-dimethylethanolamine was used for the reaction below.

To a solution of compound 15-A (200 mg, 0.59 mmol) in THF (2 mL) was added dropwise NaHMDS (0.59 mL, 0.59 mmol) at −78° C. The reaction mixture was stirred at −78° C. for 10 min, and then the resulting reaction mixture was transferred via a cannula to a solution of 4-nitrophenyl chloroformate (143 mg, 0.71 mmol) in THF (1 mL) at −78° C. The reaction mixture was allowed to warmed to rt and stirred for 30 min. The reaction mixture was then cooled to −78° C., and sodium N,N-dimethylethanolamine solution (1.4 mL, 1.4 mmol, 1 M in THF) was added. The reaction mixture was allowed to warm to rt and stirred for 30 min. Water (5 mL) was added, and the reaction mixture was extracted with ethyl acetate (2×20 mL). The combined organic layers were concentrated under reduced pressure, and the crude product was purified by Flash Chromatography (ethyl acetate/methanol/triethylamine:=100/5/1). The resulting yellow oil was further purified by prep-HPLC to give compound 15 (66 mg, 30%) as a white solid.

MS calculated for ($C_{24}H_{33}N_3O_3$)$^+$: 411; MS found, (M+1): 412. $^1$H NMR (300 MHz, $CD_3OD$) δ 7.79 (d, J=8.7 Hz, 1H), 6.7 (d, J=2.4 Hz, 1H), 6.66 (dd, J=2.4 and 8.7 Hz, 1H), 4.4 (m, 3H), 3.75 (m, 1H), 3.0 (m, 3H), 2.87 (m, 2H), 2.8 (m, 2H), 2.7 (m, 3H), 2.5 (m, 3H), 2.29 (s, 6H), 2.14 (m, 1H), 1.85 (m, 2H), 1.61-1.23 (m, 5H), 1.1 (m, 1H), 0.94 (t, J=7.2 Hz, 3H).

Example 6

Preparation of Compound 16

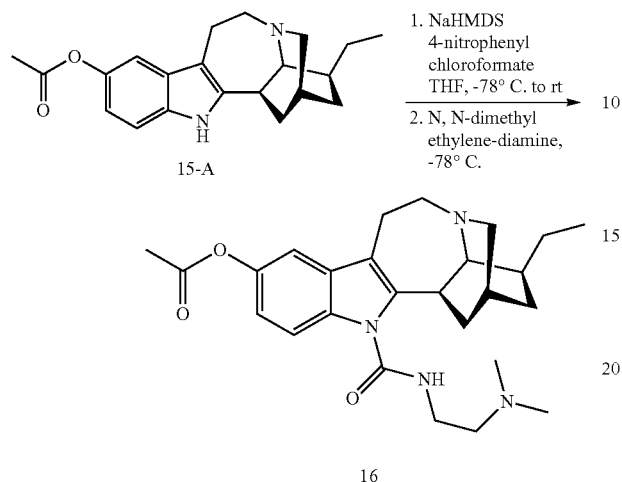

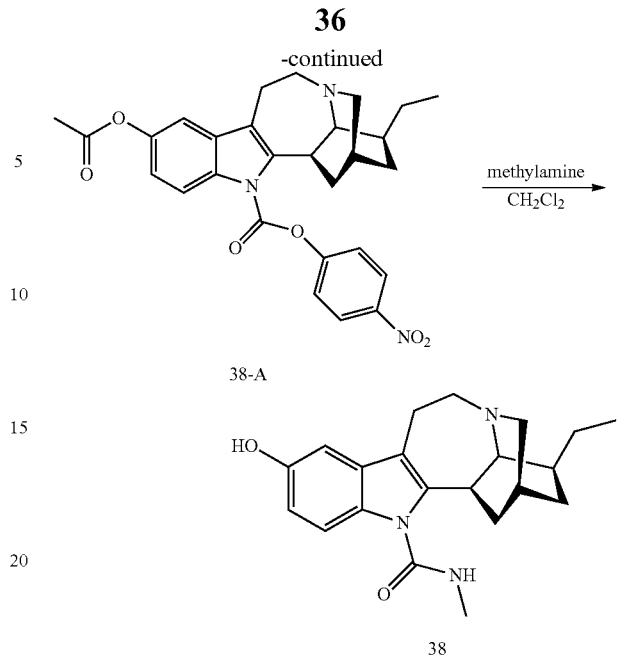

To a solution of compound 15-A (310 mg, 0.92 mmol) in THF (3 mL) was added dropwise NaHMDS (0.87 mL, 0.87 mmol) at −78° C. The reaction mixture was stirred at −78° C. for 10 min, and then the resulting reaction mixture was transferred via a cannula to a solution of 4-nitrophenyl chloroformate (185 mg, 0.92 mmol) in THF (1 mL) at −78° C. The reaction mixture was allowed to warm to rt and stirred for 30 min. The reaction mixture was recooled to −78° C., and N,N-dimethyl ethylenediamine (79 mg, 0.9 mmol) was added. The reaction mixture was warmed to rt and stirred for 30 min. Water (5 mL) was added, and the reaction mixture was extracted with ethyl acetate (2×20 mL). The combined organic layers were concentrated under reduced pressure, and the crude product was purified by Flash Chromatogaphy (ethyl acetate/methanol/triethylamine:=100/5/1). The resulting yellow oil was further purified by prep-HPLC to give compound 16 (50 mg, 14%) as a white solid.

MS calculated for $(C_{26}H_{36}N_4O_3)^+$: 452; MS found, (M+1): 453. $^1$H NMR (300 MHz, CD$_3$OD) δ 7.5 (d, J=8.7 Hz, 1H), 7.12 (d, J=2.4 Hz, 1H), 6.8 (dd, J=2.4 and 8.7 Hz, 1H), 3.5 (m, 3H), 3.4 (m, 1H), 3.2 (m, 2H), 3.0 (m, 3H), 2.8 (m, 1H), 2.6 (m, 3H), 2.3 (s, 6H), 2.27 (s, 3H), 2.14 (m, 1H), 1.85 (m, 2H), 1.61-1.23 (m, 5H), 1.1 (m, 1H), 0.94 (t, J=6.9 Hz, 3H).

a) Preparation of Compound 38-A

To a solution of compound 15-A (42 mg, 012 mmol) in THF (1 mL) was added dropwise NaHMDS (0.14 mL, 0.14 mmol) at −78° C. The reaction mixture was stirred at −78° C. for 10 min and then 4-nitrophenyl chloroformate (27 mg, 0.14 mmol) was added at −78° C. The reaction mixture was allowed to warm to rt and stirred for 1 h. Saturated NaHCO$_3$ solution (5 mL) was added, and the reaction mixture was extracted with ethyl acetate (2×10 mL). The combined organic layers were concentrated under reduced pressure. The crude product was purified by chromatography on silica gel (ethyl acetate/hexane=1/1) to give compound 38-A (20 mg) as a yellow oil in 33% yield.

MS calculated for $(C_{28}H_{29}N_3O_6)^+$: 503; MS found, (M+1): 504.

b) Preparation of Compound 38

A reaction mixture of compound 2 (150 mg, 0.3 mmol) and methylamine (1 mL, 33 wt % in ethanol) in CH$_2$Cl$_2$ (5 mL) was stirred at rt for 1 h. The reaction mixture was washed with saturated NaHCO$_3$ solution, and the aqueous layer was extracted with ethyl acetate (2×20 mL). The combined organic extracts were concentrated under reduced pressure. The crude product was purified by chromatography on silica gel (ethyl acetate/methanol/triethylamine: 100/2/1) to give compound 3 (80 mg) as a yellow oil in 80% yield.

MS calculated for $(C_{21}H_{27}N_3O_2)^+$: 353; MS found, (M+1): 354.

Example 7

Preparation of Compound 38

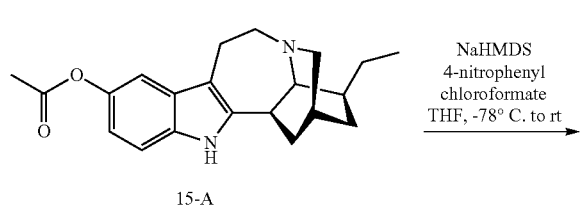

Example 8

Preparation of Compound 18

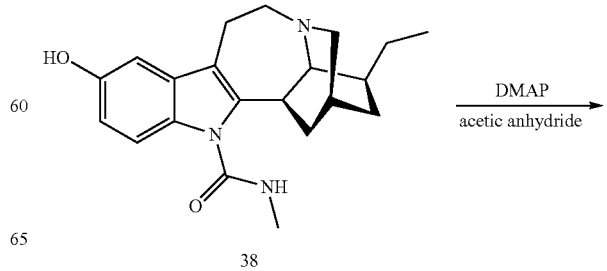

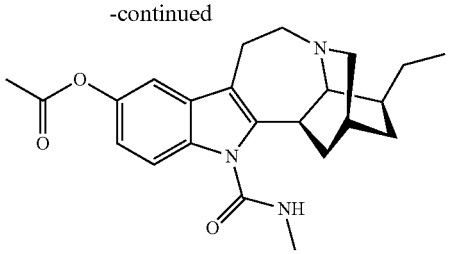

18

A reaction mixture of compound 38 (80 mg, 0.22 mmol) and DMAP (10 mg, 0.09 mmol) in acetic anhydride (3 mL) was heated at 40° C. for 16 h. The acetic anhydride was co-evaporated with toluene at 40° C. under reduced pressure. The residue was dissolved in ethyl acetate (50 mL), and the resulting solution was stirred with saturated NaHCO$_3$ solution (50 mL) at rt for 30 min. The organic phase was separated and concentrated under reduced pressure. The crude product was purified by chromatography on silica gel (ethyl acetate/methanol/triethylamine:=100/2/1) to afford a crude residue, which was further purified by preparative HPLC give compound 18 (50 mg, 60%) as a yellow solid.

MS calculated for $(C_{23}H_{29}N_3O_3)^+$: 395; MS found, (M+1): 396. $^1$H NMR (300 MHz, CD$_3$OD) δ 7.44 (d, J=8.7 Hz, 1H), 7.13 (d, J=2.4 Hz, 1H), 6.7 (dd, J=2.4 and 8.7 Hz, 1H), 3.2 (m, 1H), 3.05 (m, 4H), 2.98 (s, 3H), 2.95 (m, 2H), 2.83 (m, 1H), 2.6 (m, 1H), 2.27 (s, 3H), 2.14 (m, 1H), 1.88 (m, 2H), 1.64-1.45 (m, 4H), 1.23 (m, 1H), 0.92 (t, J=7.2 Hz, 3H).

Example 9

Preparation of Compound 31

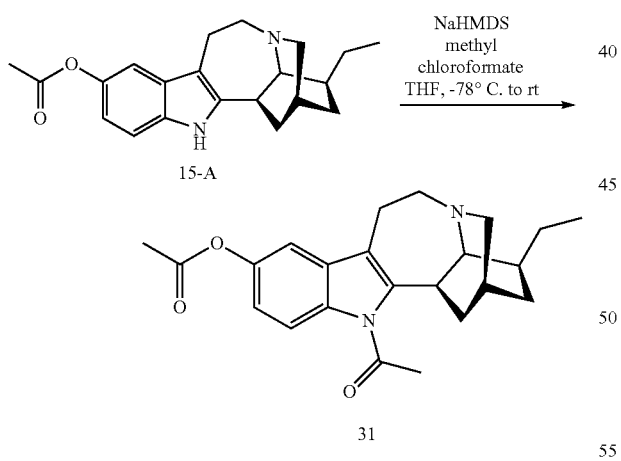

To a solution of compound 15-A (200 mg, 0.59 mmol) in THF (2 mL) was added dropwise NaHMDS (0.68 mL, 0.68 mmol) at −78° C. The reaction mixture was stirred at −78° C. for 10 min, and then methyl choroformate (78.6 uL, 0.68 mmol) was added at −78° C. The reaction mixture was allowed to warm to rt and stirred for 1 h. Saturated NaHCO$_3$ solution (5 mL) was added, and the reaction mixture was extracted with ethyl acetate (2×20 mL). The combined organic extracts were concentrated under reduced pressure to afford a crude product which was purified by preparative-HPLC to give compound 31 (116 mg, 55%) as a white solid.

MS calculated for $(C_{23}H_{28}N_2O_4)^+$: 396; MS found, (M+1): 397. $^1$H NMR (400 MHz, CD$_3$OD) δ 7.95 (d, J=9.2 Hz, 1H), 7.06 (d, J=1.2 Hz, 1H), 6.7 (dd, J=9.2 Hz, J=1.2 Hz, 1H), 4.84 (s, 3H), 3.8 (m, 1H), 3.1 (m, 3H), 2.99 (m, 2H), 2.8 (m, 1H), 2.68 (m, 1H), 2.15 (s, 3H), 2.14 (m, 1H), 1.85 (m, 2H), 1.61 (m, 2H), 1.58 (m, 1H), 1.46 (m, 1H), 1.23 (m, 1H), 0.94 (t, J=7.2 Hz, 3H).

Example 10

Preparation of Compound 39

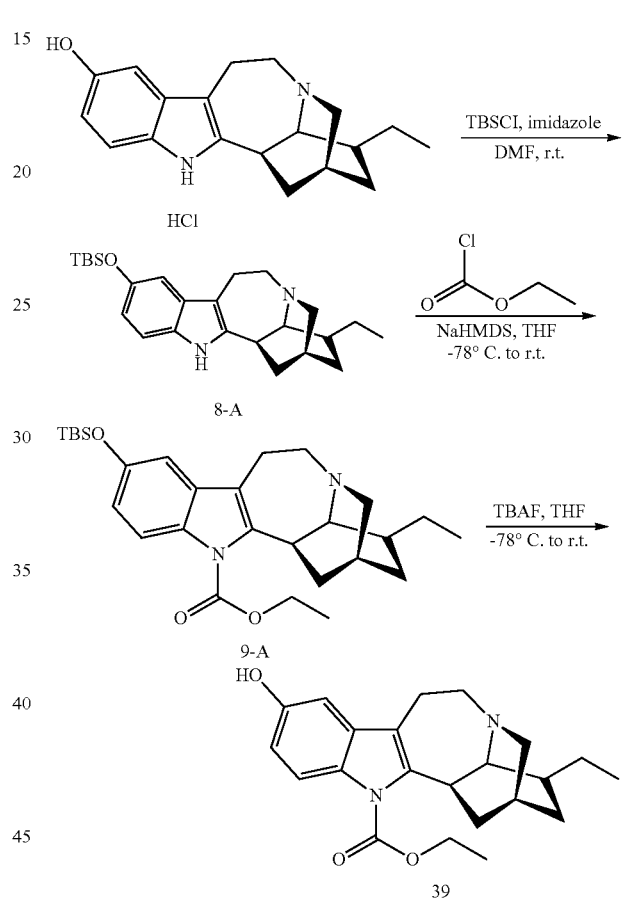

a) Preparation of TBS-Noribogaine 8-A

A suspension of noribogaine hydrochloride (852 mg, 2.56 mmol), TBS-Cl (444 mg, 2.94 mmol) and imidazole (227 mg, 3.33 mmol) in DMF (6 mL) was stirred at room temperature for 20 h. The resulting clear solution was diluted with 10% 2-propanol/dichloromethane and washed with water and brine. The aqueous phase was extracted with EtOAc. The combined organic extracts were concentrated and purified by column chromatography (EtOAc/Hexanes, v/v, 2/1) to give compound 8-A (911 mg, 87%) as a white solid.

MS calculated for $(C_{25}H_{38}N_2OSi)$: 410; MS found, (M+1): 411.

b) Preparation of Compound 9-A

NaHMDS (0.9 mL, 1.0 M solution in THF, 0.9 mmol) was added into the solution of compound 8-A (246 mg, 0.6 mmol) in THF (6 mL) at −78° C. The resulting solution was stirred for 15 min at −78° C. before ethyl chloroformate (0.12 mL, 1.2 mmol) was added. The reaction mixture was warmed up to room temperature and stirred for 1 hour, then it was partitioned between EtOAc and water. The organic layer was washed with brine and dried over Na$_2$SO$_4$. The crude product was obtained as a pale yellow oil after concentration, which was used in the next step without further purification.

MS calculated for (C$_{28}$H$_{42}$N$_2$O$_3$Si): 482; MS found, (M+1): 483.

c) Preparation of Compound 39

TBAF (1.5 mL, 1.0 M solution in THF) was added into a solution of compound 9-A (crude, ca. 0.6 mmol) in THF (12 mL) at −78° C. The resulting solution was stirred for 20 min at −78° C. before it was allowed to warm to room temperature. After one hour, the reaction mixture was diluted with 10% 2-propanol/dichloromethane and washed with water and brine. The aqueous phase was extracted with EtOAc. The combined organic layers were concentrated and purified by column chromatography (dichloromethane/MeOH, v/v, 10/1) to give compound 39 (187 mg, 85% over two steps) as a white solid.

MS calculated for (C$_{22}$H$_{28}$N$_2$O$_3$): 368; MS found, (M+1): 369. $^1$H NMR (300 MHz, CD$_3$OD) δ 7.83 (d, 1H), 6.82 (s, 1H), 6.78 (d, 1H), 4.49 (q, 2H), 4.08 (dd, 1H), 3.65-3.92 (m, 2H), 3.40-3.62 (m, 2H), 3.15-3.20 (m, 1H), 2.95-3.07 (m, 2H), 2.42-2.62 (m, 1H), 2.20 (bs, 1H), 1.80-2.10 (m, 2H), 1.40-1.80 (m, 4H), 1.48 (t, 3H), 1.05 (t, 3H).

Example 11

Preparation of Compound 32

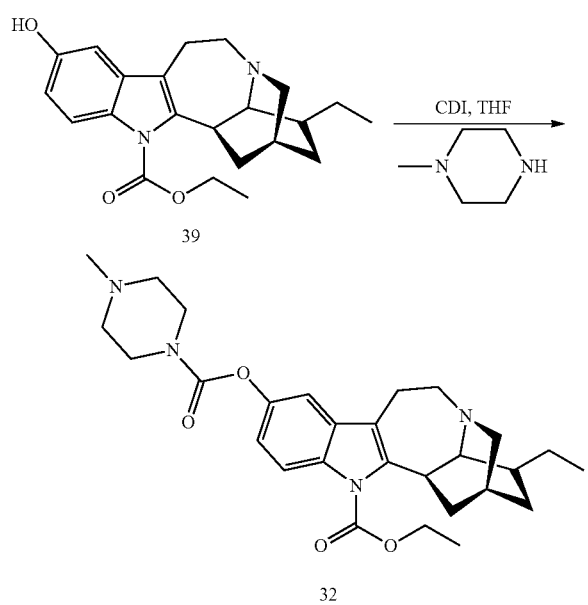

A solution of compound 39 (137 mg, 0.37 mmol) and CDI (181 mg, 1.12 mol) in THF (10 mL) was stirred at 50° C. for two hours. The mixture was then cooled to room temperature, and N-methylpiperizine (0.27 mL, 0.24 mmol) was added. After one hour, the reaction mixture diluted with 10% 2-propanol/dichloromethane and washed with water and brine. The aqueous phase was extracted with EtOAc. The combined organic extracts were concentrated and purified by preparative-HPLC to give compound 32 as the hydrochloride salt (159 mg, HCl salt, 81%) as a white solid.

MS calculated for (C$_{28}$H$_{38}$N$_4$O$_4$): 494; MS found, (M+1): 495. $^1$H NMR (400 MHz, CD$_3$OD) δ 8.07 (d, 1H), 7.35 (s, 1H), 7.09 (d, 1H), 4.57 (q, 2H), 4.40-4.60 (m, 1H), 4.25-4.40 (m, 1H), 4.12 (dd, 1H), 3.80-3.92 (m, 1H), 3.84 (s, 1H), 3.42-3.62 (m, 5H), 3.16-3.42 (m, 5H), 2.98 (s, 3H), 2.57 (td, 1H), 2.24 (bs, 1H), 1.98-2.11 (m, 2H), 1.50-1.82 (m, 3H), 1.42-1.50 (m, 2H), 1.51 (t, 3H), 1.05 (t, 3H).

Example 12

Preparation of Compound 40

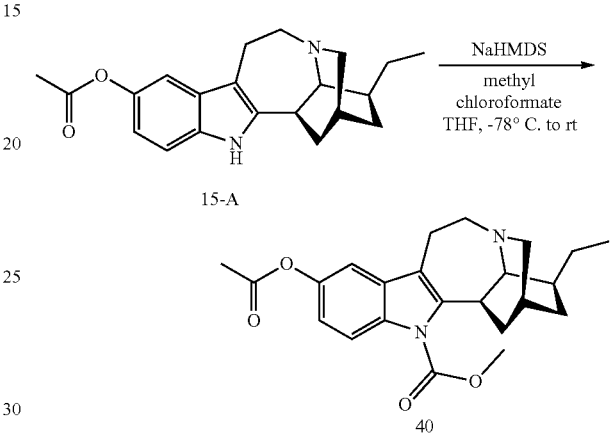

To a solution of compound 15-A (200 mg, 0.59 mmol) in THF (2 mL) was added dropwise NaHMDS (0.68 mL, 0.68 mmol) at −78° C. The reaction mixture was stirred at −78° C. for 10 min, and then methyl chloroformate (78.6 μL, 0.68 mmol) was added at −78° C. The reaction mixture was allowed to warm to rt and stirred for 1 h. Saturated NaHCO$_3$ solution (5 mL) was added, and the reaction mixture was extracted with ethyl acetate (2×20 mL). The combined organic extracts were concentrated under reduced pressure to afford a crude product which was purified by preparative-HPLC to give compound 40 (116 mg, 55%) as a white solid.

MS calculated for (C$_{23}$H$_{28}$N$_2$O$_4$)$^+$: 396; MS found, (M+1): 397. $^1$H NMR (400 MHz, CD$_3$OD) δ 7.95 (d, J=9.2 Hz, 1H), 7.06 (d, J=1.2 Hz, 1H), 6.7 (dd, J=9.2 Hz, J=1.2 Hz, 1H), 4.84 (s, 3H), 3.8 (m, 1H), 3.1 (m, 3H), 2.99 (m, 2H), 2.8 (m, 1H), 2.68 (m, 1H), 2.15 (s, 3H), 2.14 (m, 1H), 1.85 (m, 2H), 1.61 (m, 2H), 1.58 (m, 1H), 1.46 (m, 1H), 1.23 (m, 1H), 0.94 (t, J=7.2 Hz, 3H).

Example 13

Preparation of Compound 36

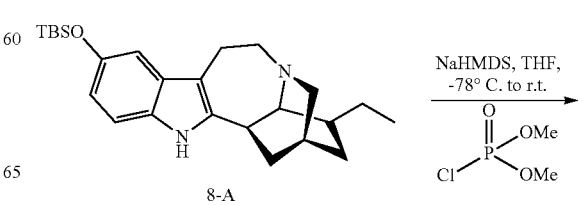

-continued

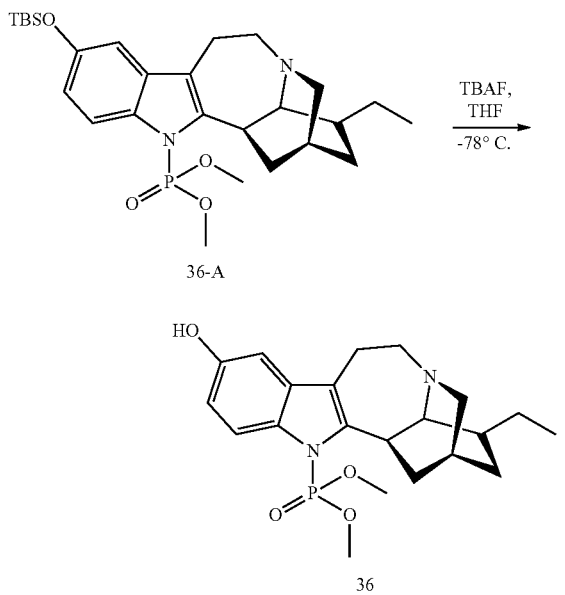

a) Preparation of Compound 36-A

NaHMDS (1.05 mL, 1.0 M solution in THF) was added into a solution of TBS-noribogaine 8-A (288 mg, 0.7 mmol) in 8 mL of THF at −78° C. The resulting solution was stirred for 10 min at −78° C. before a solution of chlorodimethyl phosphate (0.15 mL, 1.4 mmol) in 2 mL of THF was added dropwise. The reaction mixture was allowed to warm to room temperature and stirred for 1 hour, before it was diluted with 5% 2-propanol/dichloromethane and washed with water and brine. The aqueous phase was extracted with EtOAc. The combined organic extracts were concentrated and purified by column chromatography (EtOAc/Hexanes, v/v, 2/1 to pure EtOAc). The desired product compound 36-A (305 mg, 84%) was obtained as a white solid.

MS calculated for ($C_{27}H_{43}N_2O_4PSO$): 518; MS found, (M+1): 519.

b) Preparation of Compound 36

TBAF (1.1 mL, 1.0 M solution in THF) was added into a solution of compound 36-A (305 mg, 0.59 mmol) in 8 mL of THF at −78° C. The resulting solution was stirred for 40 min at −78° C. before it was quenched by addition of 2 mL of 1N aqueous HCl. The reaction mixture was diluted with 5% 2-propanol/dichloromethane and washed with water and brine. The aqueous phase was extracted with EtOAc. The combined organic layers were concentrated and purified by column chromatography (dichloromethane/2-propanol, v/v, 15/1 to 10/1) and then preparative-HPLC to give pure compound 36 as the hydrochloride salt (220 mg, HCl salt, 85%) as a white solid.

MS calculated for ($C_{21}H_{29}N_2O_4P$): 404; MS found, (M+1): 405. $^1$H NMR (300 MHz, CDCl$_3$) δ 10.38 (bs, 1H), 7.45 (d, 1H), 6.97 (s, 1H), 6.91 (d, 1H), 3.98-4.15 (m, 1H), 3.40-3.85 (m, 10H), 2.70-3.20 (m, 3H), 2.40-2.60 (m, 1H), 2.18 (bs, 1H), 1.72-2.05 (m, 4H), 1.38-1.50 (m, 2H), 0.95 (t, 3H).

Example 14

Preparation of Compound 41

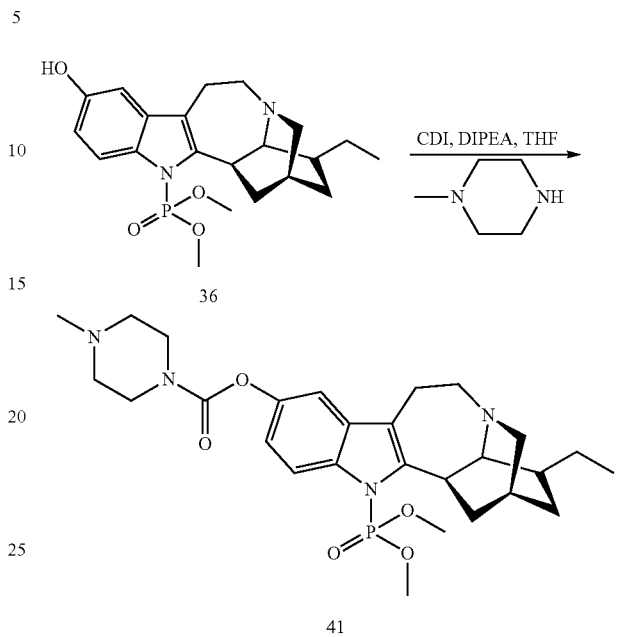

A solution of compound 36 (44 mg, 0.11 mmol), CDI (54 mg, 0.33 mol) and one drop of DIPEA in 2 mL of THF was stirred at 50° C. for two hours, before it was cooled down to room temperature. N-methylpiperizine (3 drops) was added. After one hour, the reaction mixture was concentrated and purified by preparative TLC (dichloromethane/MeOH/triethylamine, v/v, 200/20/1). Pure compound 41 (28 mg, 48%) was obtained as a white solid.

MS calculated for ($C_{27}H_{39}N_4O_5P$): 530; MS found, (M+1): 531. $^1$H NMR (300 MHz, CDCl$_3$) δ 7.95 (d, 1H), 7.13 (s, 1H), 6.95 (d, 1H), 3.65-3.82 (m, 8H), 3.55-3.65 (m, 3H), 3.47 (s, 1H), 3.40-3.45 (m, 1H), 2.96-3.40 (m, 5H), 2.72-2.95 (m, 1H), 2.40-2.70 (m, 4H), 2.35 (s, 3H), 2.08-2.25 (m, 1H), 1.78-1.95 (m, 2H), 1.38-1.70 (m, 2H), 1.15-1.20 (m, 2H), 0.89 (t, 3H).

Example 15

The following example illustrates how to treat an opioid addicted patient having an immediate craving for the opioid. In particular, a 65 kg cocaine addicted male patient presenting with an immediate craving for a cocaine "fix" is administered a bolus comprising 0.1% weight/volume of a compound of this invention in sterile buffered saline. The aqueous composition is administered in an i.v. format and the serum concentrations of the compound of this invention and noribogaine which is produced by in vivo cleavage of the compound of this invention are monitored. A sufficient amount of the compound is administered until a therapeutic serum concentration of the compound and or noribogaine is achieved. The patient is then monitored until the craving is diminished or relieved.

Example 16

The following example illustrates how to treat severe pain in a patient. In particular, a 80 kg male patient presenting severe trauma due to several gunshots to the chest and legs is administered a bolus comprising 1 gm of a compound of this invention in 10 mL of sterile buffered saline. The aqueous composition is injected into the patient to provide immediate analgesia for the pain. A transdermal patch is then placed on the patient's back. The patch contains a sufficient amount of the compound in a sustained release form wherein the amount of noribogaine released is sufficient to maintain serum concentration of the compound or noribogaine which is produced by in vivo cleavage of the compound of this invention in the patient for a period of 48 hours.

Example 17

Tablet Formulation

The following ingredients are mixed intimately and pressed into single scored tablets.

| Ingredient | Quantity per tablet, mg |
| --- | --- |
| Compound of Formula I | 40 |
| Cornstarch | 50 |
| Croscarmellose sodium | 25 |
| Lactose | 120 |
| Magnesium stearate | 5 |

Example 18

Capsule Formulation

The following ingredients are mixed intimately and loaded into a hard-shell gelatin capsule.

| Ingredient | Quantity per capsule, mg |
| --- | --- |
| Compound of Formula I | 20 |
| Lactose, spray-dried | 148 |
| Magnesium stearate | 2 |

Example 19

Suspension Formulation

The following ingredients are mixed to form a suspension for oral administration (q.s.=sufficient amount).

| Ingredient | Amount |
| --- | --- |
| Compound of Formula I | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co) | 1.0 g |
| flavoring | 0.035 mL |
| colorings | 0.5 mg |
| distilled water | q.s. to 100 mL |

Example 20

Injectable Formulation

The following ingredients are mixed to form an injectable formulation.

| Ingredient | Quantity per 20 mL |
| --- | --- |
| Compound of Formula I | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 21

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity |
| --- | --- |
| Compound of Formula I | 500 mg |
| Witepsol ® H-15 | balance |

What is claimed is:

1. A compound of Formula I:

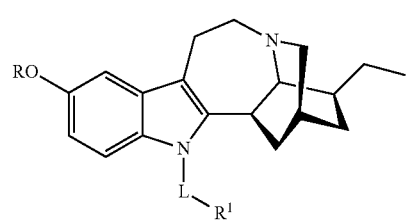

I or a pharmaceutically acceptable salt thereof
wherein
R is selected from the group consisting of hydrogen, a hydrolysable group selected from the group consisting of —C(O)R$^2$, —C(O)NR$^3$R$^4$ and —C(O)OR$^5$, where R$^2$ is selected from the group consisting of hydrogen, alkyl, substituted alkyl, alkenyl, substituted alkenyl, alkynyl and substituted alkynyl, R$^3$ and R$^4$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, R$^5$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that R is not a saccharide or an oligosaccharide;
L is selected from the group consisting of a covalent bond and a cleavable linker group;

R[1] is selected from the group consisting of hydrogen, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, provided that R[1] is not a saccharide or an oligosaccharide;

or pharmaceutically acceptable salts thereof, provided that when L is a covalent bond and R[1] is hydrogen, then R is selected from the group consisting of —C(O)NR[3]R[4] and —C(O)OR[5]; and further provided that when R is hydrogen or —C(O)R[2] and L is a covalent bond, then R[1] is not hydrogen.

2. The compound of claim 1, wherein R is hydrogen and L is a cleavable group.

3. The compound of claim 1, wherein L is a biocompatible, cleavable linking group comprising from 1 to 20 atoms selected from carbon, nitrogen, oxygen, sulfur, and phosphorus.

4. The compound of claim 1, wherein L is —C(O)—.

5. The compound of claim 1, wherein L is —C(O)O—.

6. The compound of claim 1, wherein L is —C(O)NR—, where R is hydrogen.

7. The compound of claim 1, wherein L is selected from the group consisting of —P(O)(OR[9])—O—, —O—P(S)(OR[9])—O—, —O—P(S)(SR[9])—O—, —S—P(O)(OR[9])—O—, —O—P(O)(OR[9])—S—, —S—P(O)(OR[9])—S—, —O—P(S)(OR[9])—S—, —S—P(S)(OR[9])—O—, —O—P(O)(R[9])—O—, —O—P(S)(R[9])—O—, —S—P(O)(R[9])—O—, —S—P(S)(R[9])—O—, —S—P(O)(R[9])—S—, —O—P(S)(R[9])—S— where R[9] is hydrogen or alkyl.

8. The compound of claim 1, wherein R is hydrogen, L is a covalent bond or —C(O)—, and R[1] is substituted alkyl.

9. The compound of claim 8, wherein R[1] is alkyl substituted with —NR[6]R[7] and where R[6] and R[7] are independently selected from the group consisting of hydrogen, alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

10. The compound of claim 1, wherein R is selected from the group consisting of —C(O)NR[3]R[4] and —C(O)OR[5] and R[1] is hydrogen.

11. A compound of Formula I:

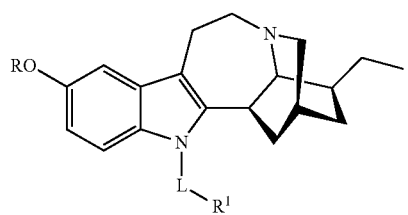

I selected from the group consisting of

| Compound No. | R | L | R[1] |
|---|---|---|---|
| 1 | —C(O)CH$_2$CH$_2$N(CH$_3$)$_2$ | —C(O)— | —CH$_2$CH$_2$N(CH$_3$)$_2$ |
| 2 | —H | —C(O)— | —CH$_2$CH$_2$N(CH$_3$)$_2$ |
| 3 | —C(O)CH$_2$CH$_2$N(CH$_3$)$_2$ | Bond | —H |
| 4 | —C(O)CH$_2$CH$_2$N(CH$_3$)$_2$ | Bond | —CH$_2$N(CH$_3$)$_2$ |
| 5 | —H | bond | —CH$_2$N(CH$_3$)$_2$ |
| 6 | —C(O)NHCH$_2$CH$_2$N(CH$_3$)$_2$ | —C(O)— | —H |
| 7 | —C(O)NHCH$_2$CH$_2$N(CH$_3$)$_2$ | —C(O)NH— | —CH$_2$CH$_2$N(CH$_3$)$_2$ |
| 8 | —H | —C(O)NH— | —CH$_2$CH$_2$N(CH$_3$)$_2$ |
| 9 | —C(O)NHCH$_2$CH$_2$N(CH$_3$)$_2$ | —C(O)NH— | —H |
| 10 | —C(O)NHCH$_2$CH$_2$N(CH$_3$)$_2$ | —C(O)— | —CH$_3$ |
| 11 | C$_6$H$_5$CH$_2$— | —C(O)— | —CH$_2$CH$_2$N(CH$_3$)$_2$ |
| 12 | —C(O)NHCH$_2$CH$_2$N(CH$_3$)$_2$ | —C(O)— | —CH$_2$CH$_2$N(CH$_3$)$_2$ |
| 13 | —C(O)NHCH$_2$CH$_2$N(CH$_3$)$_2$ | —C(O)O— | —CH$_3$ |
| 14 | —C(O)NHCH$_2$CH$_2$N(CH$_3$)$_2$ | —C(O)O— | —CH$_2$CH$_2$N(CH$_3$)$_2$ |
| 15 | —H | —C(O)O— | —CH$_2$CH$_2$N(CH$_3$)$_2$ |
| 16 | —C(O)CH$_3$, | —C(O)NH— | —CH$_2$CH$_2$N(CH$_3$)$_2$ |
| 17 | —C(O)CH$_3$, | —C(O)NH— | —H |
| 18 | —C(O)CH$_3$, | —C(O)NH— | —CH$_3$ |
| 19 | —C(O)OCH$_3$, | —C(O)NH— | —CH$_2$CH$_2$N(CH$_3$)$_2$ |
| 20 | —C(O)OCH$_3$, | —C(O)NH— | —H |
| 21 | —C(O)NHCH$_2$CH$_2$N(CH$_3$)$_2$ | —C(O)NH— | —CH$_2$-morpholinyl |
| 22 | —H | —C(O)NH— | —CH$_2$-morpholinyl |

-continued
| Compound No. | R | L | R¹ |
|---|---|---|---|
| 23 | —C(O)NHCH₂CH₂N(CH₃)₂ | —C(O)NH— | 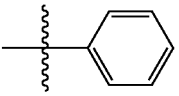 [SMILES: *c1ccccc1] |
| 24 | —C(O)NHCH₂CH₂N(CH₃)₂ | —C(O)— | 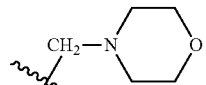 |
| 25 | —H | —C(O)— | 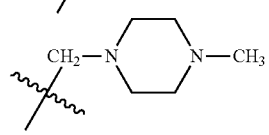 |
| 26 | —C(O)NHCH₂CH₂N(CH₃)₂ | —C(O)— | 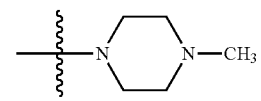 |
| 27 | —C(O)NHCH₂CH₂N(CH₃)₂ | —C(O)O— | 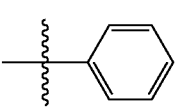 [SMILES: *c1ccccc1] |
| 28 | —C(O)NHCH₃ | —C(O)— | 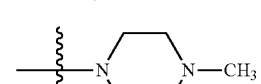 |
| 29 | —H | —C(O)— | 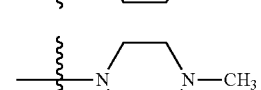 |
| 30 | 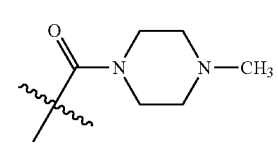 [SMILES: *C(=O)N1CCN(C)CC1] | —C(O)NH— | —CH₂CH₂N(CH₃)₂ |
| 31 | —C(O)CH₃, | —C(O)O— | —CH₃ |
| 32 | 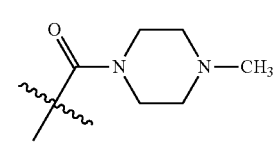 | —C(O)O— | —CH₂CH₃ |
| 33 | —C(O)CH₃, | —P(O)(OH)—O— | —H |
| 34 | —C(O)CH₃, | —P(O)(OCH₃)—O— | —CH₂CH₂N(CH₃)₂ |
| 35 | —H | —P(O)(OH)—O— | —H |
| 36 | —H | —P(O)(OCH₃)—O— | —CH₃ |
| 37 | —C(O)NHCH₂CH₂N(CH₃)₂ | —P(O)(OCH₃)—O— | —CH₃ |
| 38 | —H | —C(O)NH— | —CH₃ |
| 39 | —H | —C(O)O— | —CH₂CH₃ |
| 40 | —H | —C(O)— | 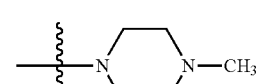 |
| 41 | 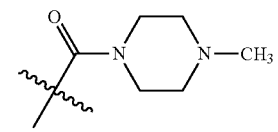 [SMILES: *C(=O)N1CCN(C)CC1] | —P(O)(OCH₃)—O— | —CH₃ |
or a pharmaceutically acceptable salt thereof.

12. A composition comprising a compound of claim 1 and a pharmaceutically acceptable excipient.

13. A method for treating a pain in a patient which method comprises administering to said patient a compound of claim 1.

14. A method for treating stress in a patient which method comprises administering to said patient a compound of claim 1.

15. The method of claim 14, wherein the stress is post traumatic stress disorder.

16. The compound of claim 1, wherein R is hydrogen.

17. The compound of claim 1, wherein L is a covalent bond and $R^1$ is hydrogen.

18. A compound of Formula I:

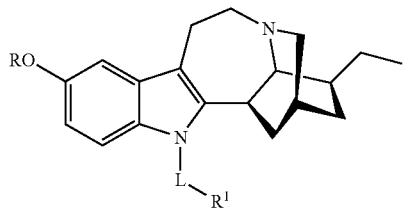

I or a pharmaceutically acceptable salt thereof wherein

R is selected from the group consisting of a hydrolysable group selected from the group consisting of —C(O)$R^2$, —C(O)N$R^3R^4$ and —C(O)O$R^5$, where $R^2$ is selected from the group consisting of hydrogen, alkyl, substituted alkyl, alkenyl, substituted alkenyl, alkynyl and substituted alkynyl, $R^3$ and $R^4$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, $R^5$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that R is not a saccharide or an oligosaccharide;

L is selected from the group consisting of a covalent bond and a cleavable linker group; and $R^1$ is alkyl.

* * * * *